(12) United States Patent
Tsunoda

(10) Patent No.: US 9,212,983 B2
(45) Date of Patent: Dec. 15, 2015

(54) SYSTEM AND METHOD FOR DETECTING AEROSOL PARTICLES IN A ATMOSPHERE AND COUNTING AEROSOL PARTICLES WITH RESPECT TO EACH PARTICLE SIZE

(75) Inventor: Chiryo Tsunoda, Kokubunji (JP)

(73) Assignee: RION CO., LTD., Tokyo (JP)

( * ) Notice: Subject to any disclaimer, the term of this patent is extended or adjusted under 35 U.S.C. 154(b) by 609 days.

(21) Appl. No.: 13/605,183

(22) Filed: Sep. 6, 2012

(65) Prior Publication Data
US 2013/0060509 A1 Mar. 7, 2013

Related U.S. Application Data

(60) Provisional application No. 61/531,702, filed on Sep. 7, 2011.

(51) Int. Cl.
| | |
|---|---|
| G01N 15/02 | (2006.01) |
| G01F 1/56 | (2006.01) |
| G06F 15/00 | (2006.01) |
| B03C 3/145 | (2006.01) |
| B03C 3/155 | (2006.01) |
| G01N 15/06 | (2006.01) |

(52) U.S. Cl.
CPC ............ G01N 15/0266 (2013.01); B03C 3/145 (2013.01); B03C 3/155 (2013.01); G01F 1/56 (2013.01); G01N 15/0656 (2013.01); G06F 15/00 (2013.01); B03C 2201/24 (2013.01)

(58) Field of Classification Search
CPC .................................................. G01N 15/0266
USPC .......................................................... 702/128
See application file for complete search history.

(56) References Cited

U.S. PATENT DOCUMENTS

| | | | |
|---|---|---|---|
| 5,922,976 A | * | 7/1999 | Russell et al. ............... 73/865.5 |
| 6,003,389 A | | 12/1999 | Flagan et al. |
| 6,281,972 B1 | | 8/2001 | Ebara et al. |

(Continued)

FOREIGN PATENT DOCUMENTS

JP          4710787 B2       6/2011

OTHER PUBLICATIONS

U.S. Appl. No. 13/605,236, filed Sep. 6, 2012; First Named Inventor: Chiryo Tsunoda; Title: Apparatus and Method for Counting Aerozol Particles in Atmosphere With Respect to Each Particle Size by Appropriately Setting Flow Rate Ratio of Sample Gas and Sheath Gas in DMA.

*Primary Examiner* — Bryan Bui
(74) *Attorney, Agent, or Firm* — Holtz, Holtz, Goodman & Chick PC

(57) ABSTRACT

A particle size distribution measuring system 1 sets a reference voltage in a DMA 300 to a voltage value U, and executes the classifying of aerosol particles based on electrical mobility, in an electric field to which the voltage value U is supplied. When a predetermined condition is not satisfied, an analyzing device 600 causes a sum of the voltage value for the previous classifying (previous value) and the voltage value U to be re-set in the DMA 300 and causes the classifying of the aerosol particles to be executed again. A particle measuring device 400 defines a first measurement result as a measurement result M1, and defines a result of the re-measurement as a new measurement result Mx every time the measurement is thereafter repeated. An analyzing device 600 calculates a ratio of the measurement result Mx to the measurement result M1, and confirms that the condition is satisfied when the calculation result is a prescribed value or smaller, while confirming that the condition is not satisfied when the calculation result is larger than the prescribed value.

8 Claims, 14 Drawing Sheets

(56) References Cited

U.S. PATENT DOCUMENTS

| | | |
|---|---|---|
| 6,541,266 B2 | 4/2003 | Modzelewski et al. |
| 8,919,183 B1 | 12/2014 | Dhaniyala et al. |
| 2008/0047373 A1* | 2/2008 | Ahn .............................. 73/865.5 |
| 2009/0056535 A1* | 3/2009 | Moosmuller et al. ............. 95/23 |
| 2009/0173670 A1 | 7/2009 | Okuda et al. |
| 2012/0001067 A1 | 1/2012 | Orii et al. |

* cited by examiner

| NUMBER OF CHARGES | CHARGING PROBABILITY RATIO $\alpha_p$ |
|---|---|
| $p=1$ | — |
| $p=2$ | $\alpha_2 = \dfrac{f_2(Z_1(2U))}{f_1(Z_1(2U))}$ |
| $p=3$ | $\alpha_2 = \dfrac{f_2(Z_1(2U))}{f_1(Z_1(2U))}$, $\quad \alpha_3 = \dfrac{f_3(Z_1(3U))}{f_1(Z_1(3U))}$ |
| $p=4$ | $\alpha_2 = \dfrac{f_2(Z_1(2U))}{f_1(Z_1(2U))}$, $\quad \alpha_3 = \dfrac{f_3(Z_1(3U))}{f_1(Z_1(3U))}$, <br> $\alpha_4 = \dfrac{f_4(Z_1(4U))}{f_1(Z_1(4U))} - \dfrac{f_2(Z_1(2U))}{f_1(Z_1(2U))} \cdot \dfrac{f_2(Z_1(4U))}{f_1(Z_1(4U))}$ |
| $p=5$ | $\alpha_2 = \dfrac{f_2(Z_1(2U))}{f_1(Z_1(2U))}$, $\quad \alpha_3 = \dfrac{f_3(Z_1(3U))}{f_1(Z_1(3U))}$, <br> $\alpha_4 = \dfrac{f_4(Z_1(4U))}{f_1(Z_1(4U))} - \dfrac{f_2(Z_1(2U))}{f_1(Z_1(2U))} \cdot \dfrac{f_2(Z_1(4U))}{f_1(Z_1(4U))}$, $\quad \alpha_5 = \dfrac{f_5(Z_1(5U))}{f_1(Z_1(5U))}$ |
| $p=6$ | $\alpha_2 = \dfrac{f_2(Z_1(2U))}{f_1(Z_1(2U))}$, $\quad \alpha_3 = \dfrac{f_3(Z_1(3U))}{f_1(Z_1(3U))}$, <br> $\alpha_4 = \dfrac{f_4(Z_1(4U))}{f_1(Z_1(4U))} - \dfrac{f_2(Z_1(2U))}{f_1(Z_1(2U))} \cdot \dfrac{f_2(Z_1(4U))}{f_1(Z_1(4U))}$, $\quad \alpha_5 = \dfrac{f_5(Z_1(5U))}{f_1(Z_1(5U))}$ <br> $\alpha_6 = \dfrac{f_6(Z_1(6U))}{f_1(Z_1(6U))} - \dfrac{f_2(Z_1(2U))}{f_1(Z_1(2U))} \cdot \dfrac{f_2(Z_1(6U))}{f_1(Z_1(6U))} - \dfrac{f_3(Z_1(3U))}{f_1(Z_1(3U))} \cdot \dfrac{f_3(Z_1(6U))}{f_1(Z_1(6U))}$ |
| ⋮ | ⋮ |

FIG.14

SYSTEM AND METHOD FOR DETECTING AEROSOL PARTICLES IN A ATMOSPHERE AND COUNTING AEROSOL PARTICLES WITH RESPECT TO EACH PARTICLE SIZE

BACKGROUND OF THE INVENTION

1. Field of the Invention

The present invention relates to a system and a method for detecting aerosol particles in the atmosphere and counting the aerosol particles, and more particularly, to a system and a method for counting the detected aerosol particles with respect to each particle size.

2. Description of the Related Art

In the atmosphere, "aerosol particles" which are fine liquid or solid particles are suspended. As these aerosol particles, the ISO 15900:2009 standard for differential electrical mobility analysis for aerosol particles targets at aerosol particles whose particle size is 1 nm to 1 .mu.m. To count the aerosol particles having several nm to 1 .mu.m particle sizes, an aerosol particle measuring device is used. The aerosol particle measuring device includes, for example, a differential mobility analyzer (DMA) and a condensation particle counter (CPC), or the DMA and a Faraday cup aerosol electrometer (FCAE). The CPC or the FCAE measures the aerosol particles classified out by the DMA, whereby it is possible to count the aerosol particles with respect to each particle size by using the result of the measurement.

In the case where the DMA is used for the classifying, the aerosol particles include not only singly charged aerosol particles whose particle size is relatively small but also multiply (doubly, triply, . . . ) charged aerosol particles whose particle size is relatively large. Therefore, in the measurement, it is assumed that the aerosol particles classified out by the DMA are singly charged and a lognormal distribution holds true in a relation between the particle size and quantity, and the counting result is corrected regarding the quantity of the multiply charged aerosol particles and then particle size distribution is calculated. In the correction, an approximate expression of Wiedensohler or the like is employed as an existence probability of charged number.

When aerosol in the atmosphere is measured, it is generally assumed that the particle distribution is the lognormal distribution, but actually, this is not always the case. Further, in the ordinary measurement method, since the measurement is based on the assumption that aerosol particles are singly charged, it is not known how many multiply charged aerosol particles different in particle size are actually included, which makes it difficult to obtain an accurate result.

SUMMARY OF THE INVENTION

The present invention disclosed and claimed herein, in one aspect thereof, is a particle size distribution measuring system. The system includes: a neutralizer which puts aerosol particles into a charged equilibrium state; a DMA which classifies the aerosol particles charged by the neutralizer in a predetermined electric field based on electrical mobility and which, in a state where a reference voltage supplied to form the electric field is initially set to a voltage value U, executes the first classifying of the aerosol particles is under the supplied voltage having the initially set voltage value U; an aerosol particle measuring device which measures the aerosol particles classified out by the DMA, by an electrical or/and optical measuring method and outputs a result of the measurement; and a measurement result analyzing device which confirms whether or not a predetermined condition is satisfied, based on the measurement result output by the aerosol particle measuring device, and when confirming that the condition is satisfied, calculates particle size distribution with respect to each particle size from the measurement result output by the aerosol particle measuring device. On the other hand, when confirming that the aforesaid condition is not satisfied, the measurement result analyzing device executes: causing the DMA, in a state where the voltage supplied to form the electric field is re-set to a sum of the voltage value of the voltage supplied in the previous classifying (previous value) and the voltage value U, to execute re-classifying of the aerosol particles under the supplied voltage having the re-set voltage value; causing the aerosol particle measuring device to output a first measurement result M1 which is the measurement result of the aerosol particles that the DMA classifies out under the supplied voltage having the initially set voltage value U, and to output a new measurement result Mx which is the re-measurement result of the aerosol particles that are classified out, every time the re-classifying is executed by the DMA; calculating a ratio of the measurement result Mx to the measurement result M1; confirming that the condition is not satisfied yet when the calculated ratio is larger than a prescribed value, while confirming that the condition is satisfied when the calculated ratio is equal to or smaller than the prescribed value; and when confirming that the condition is satisfied, calculating the particle size distribution with respect to each particle size from the measurement result based on a charging probability for the aerosol particles to be charged by the neutralizer.

Further scope of applicability of the present invention will become apparent from the detailed description given hereinafter. However, it should be understood that the detailed description and specific example, while indicating preferred embodiment of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIG. 14 is an explanatory chart of a relation between the number of charges on the classified aerosol particles and a charging probability ratio.

DETAILED DESCRIPTION

Figure 1:
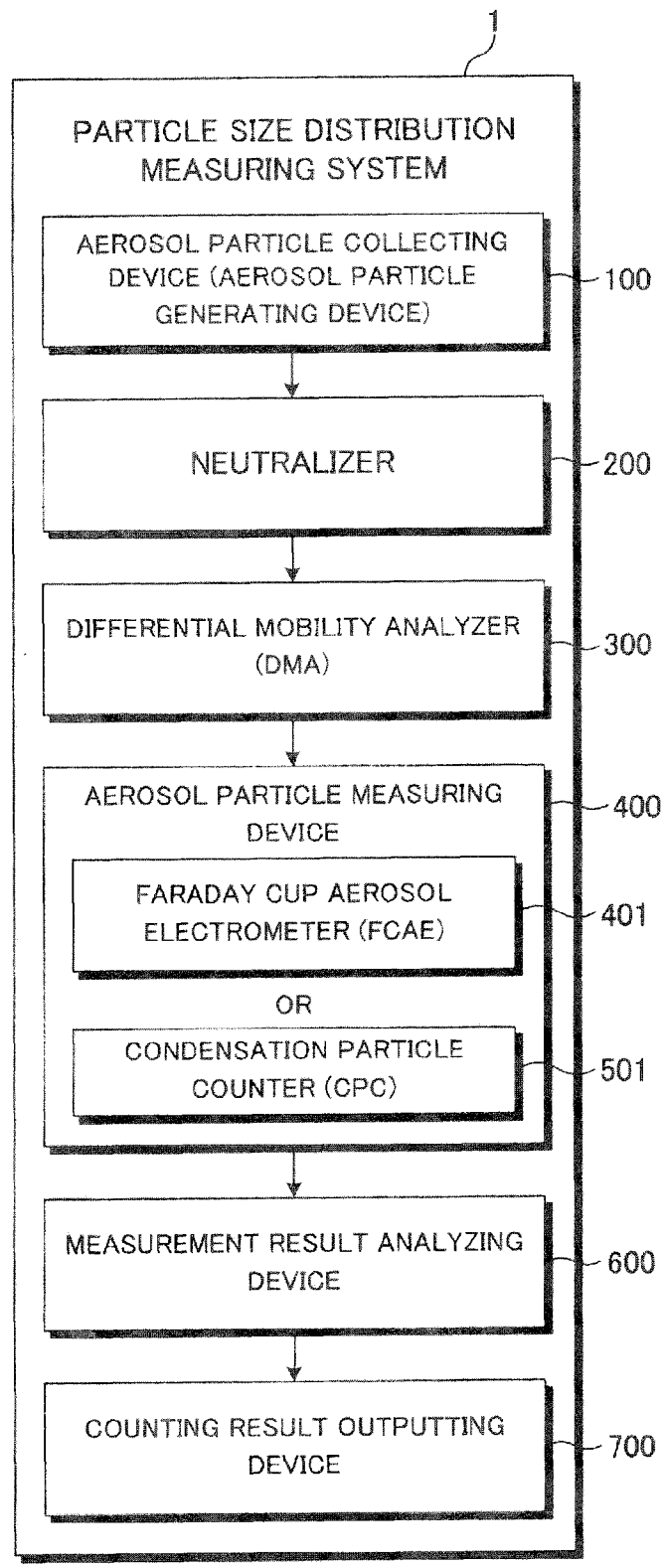
FIG. 1 is an explanatory diagram of a structure of an aerosol particle measuring device.

As shown in FIG. 1, a particle size distribution measuring system 1 includes an aerosol particle collecting device (or an aerosol particle generating device) 100, a neutralizer 200, a differential mobility analyzer (hereinafter, referred to as DMA) 300; an aerosol particle measuring device 400, and a measurement result analyzing device 600, and a counting result outputting device 700.

The aerosol particle collecting device 100 collects aerosol particles such as dust, droplets (liquid particles), and so on suspended in the atmosphere. Concretely, the aerosol particle collecting device 100 includes a dust collector which collects (catches) aerosol particles whose particle size is approximately 1 nm to approximately 1 μm.

The aerosol particle generating device 100 which is a different form from the collecting device includes a soot generator which generates soot (carbide) by utilizing a combustion process, an aerosol particle generator which generates droplets from a solvent; and so on.

Incidentally, details of particle density distribution (particle size distribution per unit volume) regarding the collected or generated dust and droplets (liquid particles) suspended in the atmosphere will be described later with reference to another drawing.

The aerosol particles collected by the aerosol particle collecting device 100 (or generated by the aerosol particle generating device 100) are next sent to the neutralizer 200.

The neutralizer 200 is a device which charges the aerosol particles collected by the aerosol collecting device 100 so that an average charge amount becomes zero (charged equilibrium state). The concrete contents approximately the aerosol particles charged by the neutralizer 200 will be further described later with reference to another drawing.

The aerosol particles charged by the neutralizer 200 (also including uncharged ones) are next sent to the DMA 300.

The DMA 300 classifies the aerosol particles charged by the neutralizer 200 according to electrical mobility. By adjusting the setting regarding the operation of the DMA 300 (for example, supplied voltage), it is possible to set the electrical mobility according to the aerosol particles being targets of the classifying. The concrete contents approximately the aerosol particles classified out by the DMA 300 will be further described later with reference to another drawing.

The aerosol particles classified out by the DMA 300 are next sent to the aerosol particle measuring device 400. Incidentally, the aerosol particles not classified out by the DMA 300 are discharged to the outside of the measuring system 1.

The aerosol particle measuring device 400 measures the number of the aerosol particles classified out by the DMA 300. The measuring device 400 includes at least one of a Faraday cup aerosol electrometer (hereinafter, referred to as FCAE) 401 and a condensation particle counter (hereinafter, referred to as CPC) 501. The FCAE 401 catches the charged aerosol particles classified out by the DMA 300 and measures a current value corresponding to the number of charges on the caught particles. Further, with the aerosol particles classified out by the DMA 300 being condensation nuclei, the CPC 501 condenses alcohol or water to grow them into large droplets, and optically detects the enlarged droplets to measure the number of the particles. The concrete contents regarding the aerosol particles measured by the FCAE 401 and the CPC 501 will be further described later with reference to another drawing.

A result of the measurement by the aerosol particle measuring device 400 is transmitted to the measurement result analyzing device 600.

The measurement result analyzing device 600 counts the number of the aerosol particles with respect to each particle size based on the data measured by the FCAE 401 or the CPC 501. A concrete counting method will be further described later with reference to another drawing. Information on the number of the aerosol particles counted by the measurement result analyzing device 600 is transmitted to the counting result outputting device 700.

Regarding the number of the aerosol particles counted by the measurement result analyzing device 600, the counting result outputting device 700 displays the number of the particles with respect to each particle size.

[Aerosol Particles in Atmosphere]

Next, the aerosol particles in the atmosphere collected by the aerosol particle collecting device 100 will be described.

Figure 2:
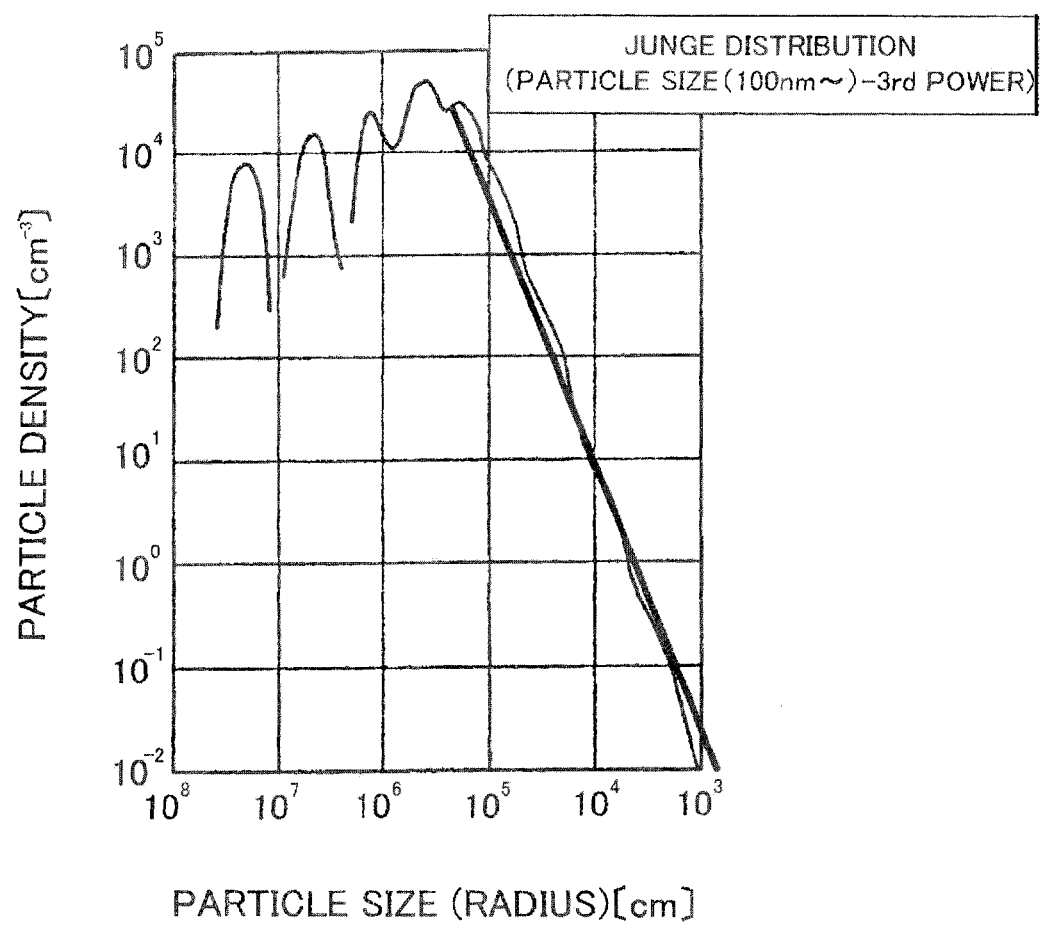
FIG. 2 is an explanatory chart of an aerosol particle density distribution (Junge distribution) in the atmosphere.

FIG. 2 is an explanatory chart of aerosol particle density distribution in the atmosphere (Reference: H. Israel, Atmospheric Electricity, Volume 1, pp. 153, 1970).

As shown in FIG. 2, as for the aerosol particles in the atmosphere, the particle density distribution thereof differs depending on particle size, and concretely, the density with respect to each particle size follows the Junge distribution. According to the Junge distribution, it is shown that the distribution of the aerosol particles whose particle size is larger than 100 nm is based on an inverse cubic size distribution law, and aerosol particles with a larger particles size are less suspended in the atmosphere. For example, the number of suspended aerosol particles smaller than 100 nm is approximately several ten thousands per cubic cm, while the number of suspended aerosol particles larger than 100 nm is only several per cubic cm. That is, the Junge distribution shows that compared with the number of aerosol particles with al 00 nm particle size (in FIG. 2, a 50 nm radius), the number of aerosol particles with a 200 nm particle size (in FIG. 2, a 100 nm radius) is approximately one tenth, and the number of aerosol particles with a 300 nm particle size (in FIG. 2, a 150 nm radius) is approximately one thirtieth, and the number of larger aerosol particles is very small based on the inverse cubic size distribution law.

Therefore, it is understood that, based on the Junge distribution shown in FIG. 2, most of the aerosol particles in the atmosphere collected by the aerosol particle collecting device 100 are aerosol particles with 100 nm or less, and the number of aerosol particles with 100 nm or more is extremely small based on the inverse cubic size distribution law. Further, aerosol particles with 200 nm or more and aerosol particles with 300 nm or more are not suspended in the atmosphere almost at all, and accordingly, are not collected almost at all by the aerosol particle collecting device 100. These also apply to the aerosol particles generated by the aerosol particle generating device 100.

[Neutralizer]

Next, it will be described that the collected or generated aerosol particles are charged by the neutralizer 200.

Figure 3:
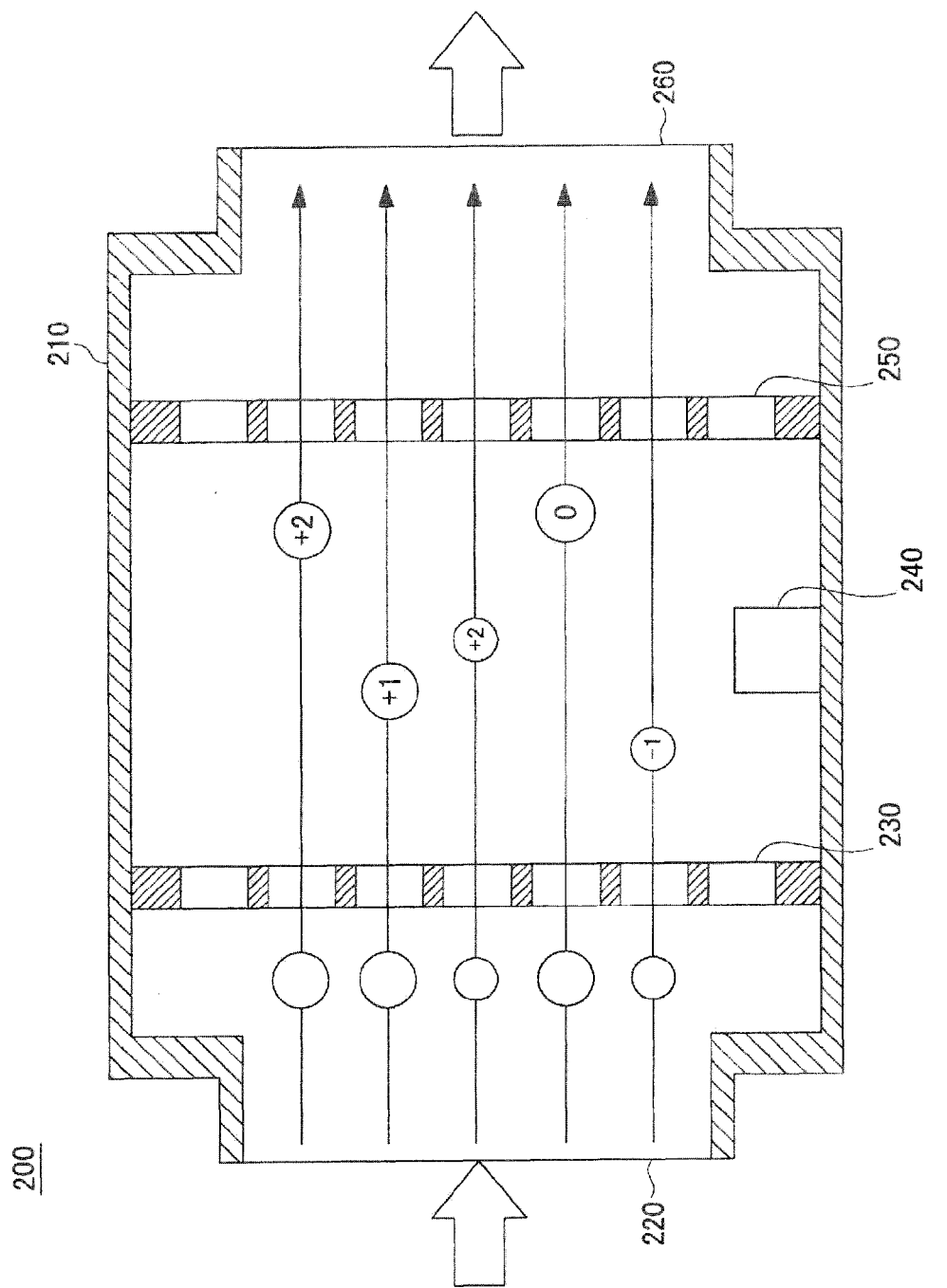
FIG. 3 is an explanatory diagram of a neutralizer.

As shown in FIG. 3, the neutralizer 200 lets the aerosol particles flow thereinto from an inflow port 220 provided in its vessel 210. The vessel 210 is formed of, for example, a SUS vessel. Further, in the vessel 210, a pair of porous plates 230, 250 is provided, for instance, and a radioactive source 240 is installed in a region between the porous plates 230, 250. As the radioactive source 240, a $^{241}$AM, $^{85}$Kr, $^{210}$Po, or the like is used. Installing the radioactive source 240 maintains the charged equilibrium state in the region between the porous plates 230, 250, and the aerosol particles are charged when passing in the region. Next, a charging probability of the aerosol particles which differs depending on each particle size will be described.

[Charging Probability Distribution]

Figure 4:
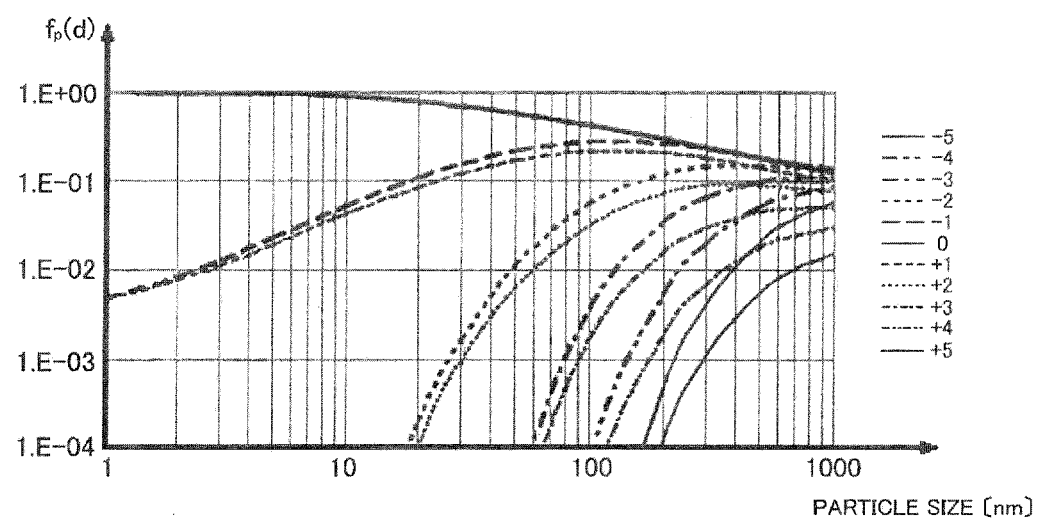
FIG. 4 is an explanatory chart of a charging probability distribution.

FIG. 4 is an explanatory chart of a charging probability distribution (ISO 15900:2009).

FIG. 4 shows charging probabilities for aerosol particles to have a charge of zero to a charged of ±5 at the charged equilibrium state. The smaller the particle size is, the less likely aerosol particles are charged, and on the contrary, the larger the particle size is, the more likely aerosol particles are charged, and further the more likely they are multiply charged.

For example, approximately 98% of aerosol particles with a 1 nm particle size are not charged and approximately another 1% and the other 1% are charged to have a charge of −1 and a charge of +1 respectively. Besides, approximately 90% or more of aerosol particles with a particle size of up to 10 nm are not charged.

For example, among aerosol particles with a 100 nm particle size, approximately 40% are not charged, approximately 30% are charged to have a charge of −1, approximately 20% are charged to have a charge of +1, approximately 6% are charged to have a charge of −2, and approximately 3% are charged to have a charge of +2. Further, among aerosol particles with a 200 nm particle size, approximately 30% are not charged, approximately 30% are charged to have a charge of −1, approximately 20% are charged to have a charge of +1, approximately 12% are charged to have a charge of −2, approximately 8% are charged to have a charge of +2, approximately 3% are charged to have a charge of −3, and approximately 2% are charged to have a charge of +3. Further, among aerosol particles with a 300 nm particle size, approximately 20% are not charged, approximately 20% are charged to have a charge of −1, approximately 15% are charged to have a charge of +1, approximately 15% are charged to have a charge of −2, approximately 9% are charged to have a charge of +2, approximately 7% are charged to have a charge of −3, approximately 3% are charged to have a charge of +3, and approximately 2% are charged to have a charge of −4.

Next, it will be described that the aerosol particles charged by the neutralizer 200 are classified by the DMA 300 will be described.

[Differential Mobility Analyzer: DMA]

Figure 5:
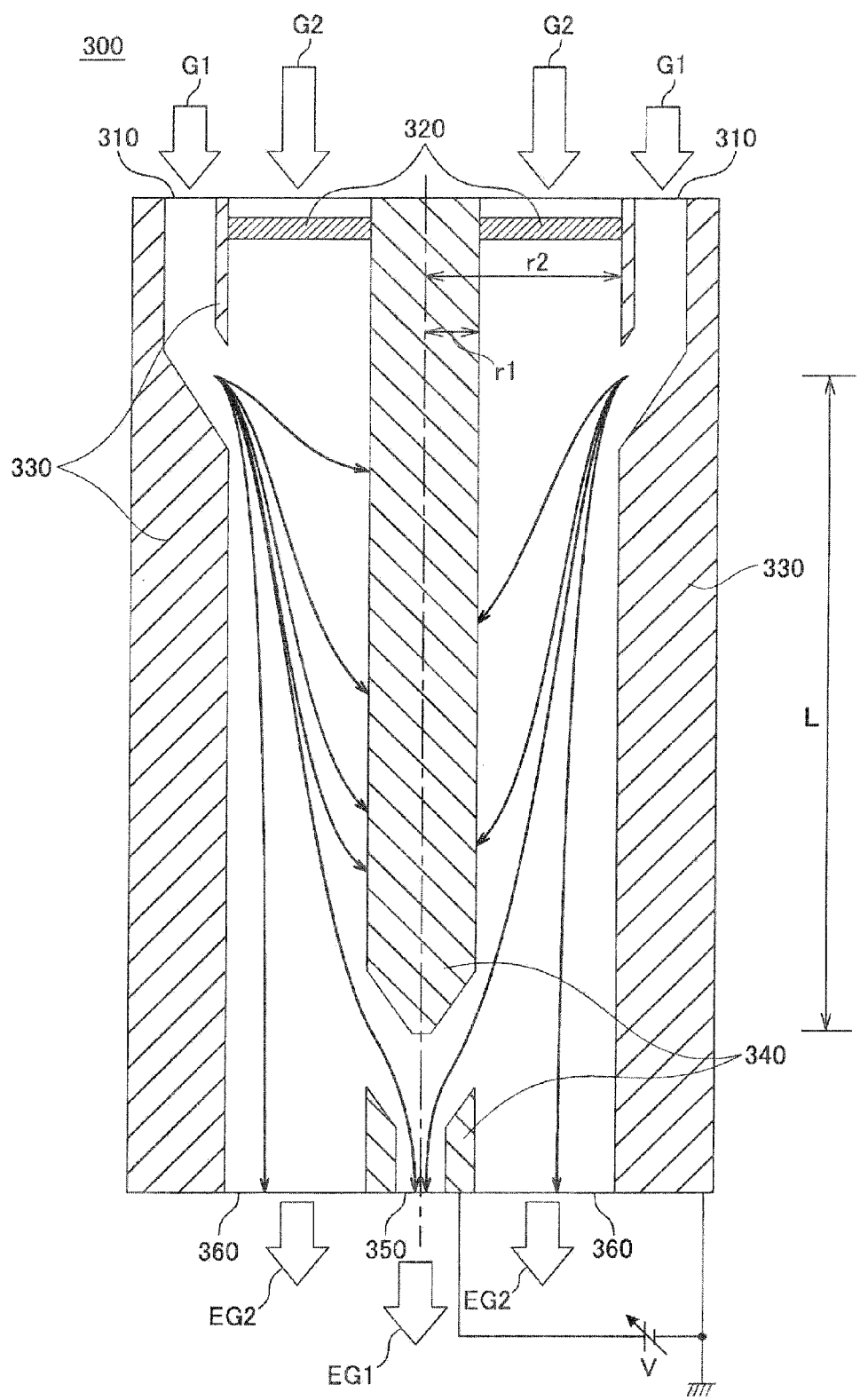
FIG. 5 is an explanatory diagram of a DMA.

As shown in FIG. 5, the DMA 300 has a dual cylindrical shape composed of an inner cylinder and an outer cylinder. The atmosphere (sample gas G1) containing the aerosol particles charged by the neutralizer 200 is made to flow with clean air (sheath gas G2). Note that a filter 320 is provided at a position preceding a position where the sheath gas G2 joins the aerosol particles, and impurities in the sheath gas G2 are removed by the filter 320.

The outer cylinder of the DMA 300 is used as an outer electrode 330 and the inner cylinder of the DMA 300 is used as an inner electrode 340. The outer electrode 330 is installed apart from a center axis of the DMA 300 by a distance $r_2$, and the inner electrode 340 is installed apart from the center axis of the DMA 300 by a distance $r_1$. A voltage V is supplied between the outer electrode 330 and the inner electrode 340. Therefore, the sample gas G1 containing the aerosol particles which flows in from the inflow port 310 flows with the sheath gas G2 in an electric field to which the voltage V is supplied.

An electrostatic force and a resistance force act on the aerosol particles moving in the sheath gas. Further, as for particles moving in a fluid while receiving an electrostatic attraction force, since the electrostatic force and the resistance force are balanced in a steady state, a constant velocity v of the particles is proportional to an electric field E, and a relation of v=ZE holds, where Z is electrical mobility.

Here, the electrical mobility Z is expressed by the following mathematical expression (1).

$$Z(d, p) = \frac{p \cdot e}{3\pi\mu_g d}\left\{1 + \frac{2l_g}{d}\left[1.165 + 0.483\exp\left(-\frac{0.997d}{2l_g}\right)\right]\right\} \quad (1)$$

In the mathematical expression (1) expressing the electrical mobility Z, p represents the number of charges on the aerosol particles, e represents the elementary charge, $\mu_g$ represents the dynamic viscosity of a gas (particle size of a gas), d represents the particle diameter particle size of the aerosol particles, and lg represents a mean free path of gas molecule.

Therefore, the charged aerosol particles flowing into the DMA 300 from its inflow port 310 move along the trajectories shown in FIG. 5 based on the electrical mobility Z. Concretely, aerosol particles with large particle sizes whose number of charges is 2 and 3 also reach an exit port 350 for classified particle together with aerosol particles with small particle sizes whose number of charges is 1 (EG1). As described above, the DMA 300 is capable of classifying out the aerosol particles based on each given electrical mobility, and classifies out not only singly charged particles but also multiply charged particles. Incidentally, the aerosol particles not classified out are discharged from an exit port 360 (EG2).

Further, the electrical mobility Z can also be derived from the structure of the DMA 300 (the radius r1 of the inner electrode, the radius $r_2$ of the outer electrode, and a distance L up to the classifying) and set items regarding the operation of the DMA 300, and is expressed by the following mathematical expression (2) when a flow rate $q_2$ of the sample gas is equal to its discharge rate $q_3$ from the exit port 350 for classified particle and a flow rate $q_1$ of the sheath gas is equal to its discharge rate $q_4$ from the exit port 360 ($q_1=q_4$, $q_2=q_3$).

$$Z_1(U) = \frac{q_1 \cdot \ln(r_2/r_1)}{2\pi \cdot L} \cdot \frac{1}{U} = A \cdot \frac{1}{U} \quad (2)$$

In the mathematical expression (2) expressing the electrical mobility Z, U represents a supplied voltage.

Therefore, the electrical mobility Z can be adjusted by the supplied voltage U if the flow rate $q_1$ of the sheath gas is constant. Note that the flow rate $q_2$ of the sample gas÷the flow rate $q_1$ of the sheath gas is called a flow rate ratio.

[Aerosol Particles Corresponding to Electrical Mobility]

Figure 6:
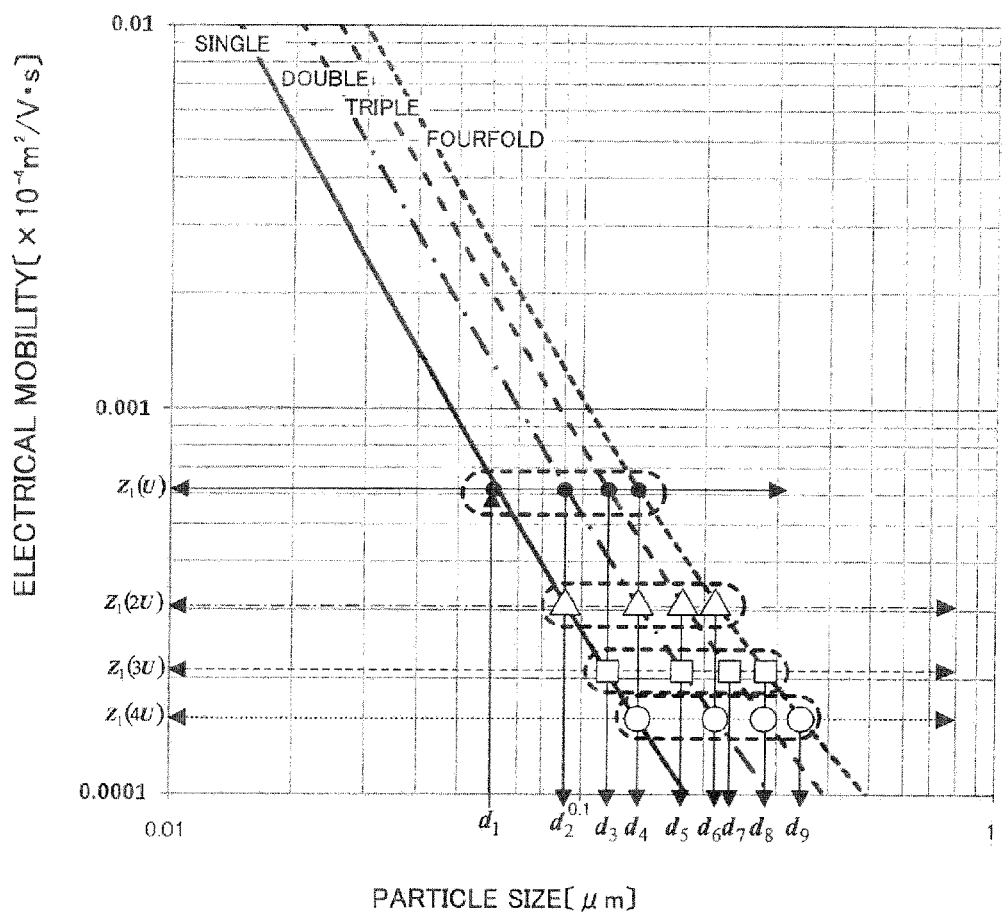
FIG. 6 is an explanatory chart of particle size and number of charges of aerosol particles that are classified out, corresponding to electrical mobility.

FIG. 6 shows an example of the electrical mobility which is found from the mathematical expression (1) and the mathematical expression (2) expressing the electrical mobility Z, in relation to the particle size, when the DMA 300 is operated. Here, the numbers of charges up to 4 are shown, and in observing the particle size distribution, there is almost no problem if the consideration is given up to approximately 4 charges.

For example, the aerosol particles classified out based on the electrical mobility Z(U) when the voltage U is supplied to the DMA 300 are represented by the four black dots (●) depicted in FIG. 6. They are not only aerosol particles with a particle size $d_1$ whose number of charges is 1, but also aerosol particles with a particle size $d_2$ whose number of charges is 2, and aerosol particles with a particle size $d_3$ whose number of charges is 3, and aerosol particles with a particle size $d_4$ whose number of charges is 4. Here, the particle size $d_1$ is approximately 60 nm, the particle size $d_2$ is approximately 90 nm, the particle size $d_3$ is approximately 115 nm, and the particle size $d_4$ is approximately 135 nm.

Next, electrical mobility when a voltage 2U twice as high as that for the aforesaid electrical mobility Z(U) is supplied to the DMA 300 in order to classify out the aerosol particles with the particle size $d_2$ and with the number of charges of 2 which are classified out based on the electrical mobility Z(U) is defined as Z(2U). The aerosol particles classified out by the DMA 300 at this time are represented by the four triangular marks (Δ) depicted in FIG. 6. They are aerosol particles with the particle size $d_2$ whose number of charges is 1, aerosol particles with the particle size $d_4$ whose number of charges is 2, aerosol particles with a particle size $d_5$ whose number of charges is 3, and aerosol particles with the particle size $d_6$ whose number of charges is 4. As for the aerosol particles whose number of charges is 2, those with the same particle size as that of the aerosol particles with the number of charges of 4 classified out based on the electrical mobility Z(U) are classified out. Note that the other particle size $d_5$ is approximately 180 nm and the other particle size $d_6$ is approximately 210 nm.

Thereafter, similarly, aerosol particles classified out based on electrical mobility Z(3U) when a voltage 3U three times as high as the voltage for the electrical mobility Z(U) is supplied to the DMA 300 are represented by the four square marks (□) depicted in FIG. 6, and aerosol particles with the same particle size $d_3$ as that of the aerosol particles with the number of charges of 3 classified out based on the electrical mobility Z(U) are classified out, and aerosol particles with the same particle size $d_5$ as that of the aerosol particles with the number of charges of 3 classified out based on the electrical mobility Z(2U) are classified out. Further, aerosol particles classified out based on electrical mobility Z(4U) when a voltage 4U four times as high as the voltage for the electrical mobility Z(U) is supplied to the DMA 300 are represented by the four white circular marks (○) depicted in FIG. 6, and aerosol particles with the same particle size $d_4$ as that of the aerosol particles with the number of charges of 4 classified out based on the electrical mobility Z(U) are classified out, and aerosol particles with the same particle size $d_6$ as that of the aerosol particles with the number of charges of 4 classified out based on the electrical mobility Z(2U) are classified out, and aerosol particles with the same particle size $d_8$ as that of the aerosol particles with the number of charges of 4 classified out based on the electrical mobility Z(3) are classified out. Note that the particle size $d_7$ is approximately 240 nm, the particle size $d_8$ is approximately 290 nm, and the particle size $d_9$ is approximately 340 nm.

The aerosol particles classified out by the DMA 300 based on the electrical mobility Z are next sent to the aerosol particle measuring device 400, where the data regarding the number of the aerosol particles are measured. Hereinafter, the FCAE 401 will be first described, and next the CPC 501 will be described.

[Faraday Cup Aerosol Electrometer: FCAE]

Figure 7:
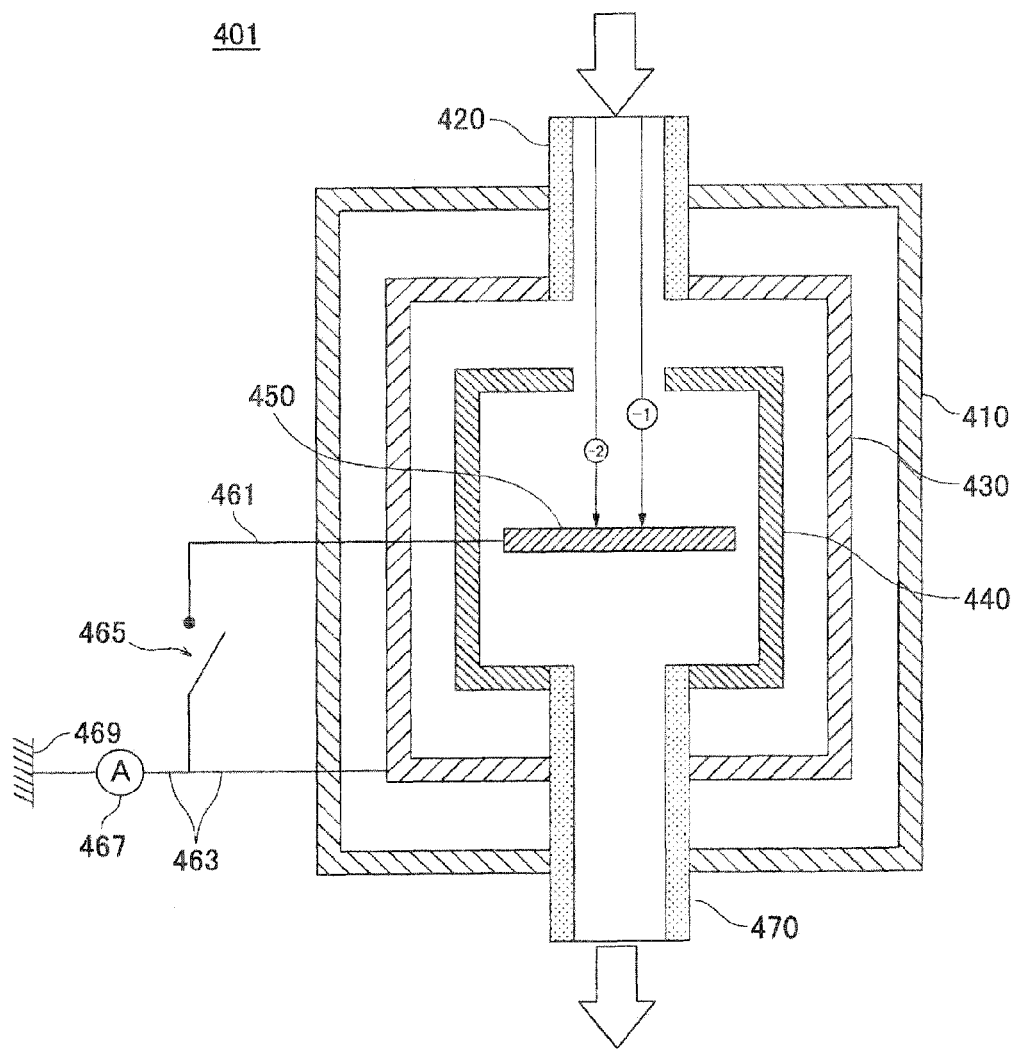
FIG. 7 is an explanatory diagram of a FCAE.

As shown in FIG. 7, the FCAE 401 lets the aerosol particles classified out by the DMA 300 flow thereinto from an inflow port 420 provided in its vessel 410. In the vessel 410, a conductive materials 430 is installed, and an insulator 440 is installed in the conductive materials 430. Further, in the insulator 440, an aerosol particle collector 450 is installed, and this collector 450 is made of conductive materials collecting (catching) the charged aerosol particles. The aerosol particle collector 450 and the conductive materials 430 are insulated from each other by the insulator 440. Further, the conductive materials 430 and a ground 469 are connected by a lead wire 463, and an ammeter 467 is installed on the lead wire 463. Further, one end of a lead wire 461 is connected to the aerosol particle collector 450, and the other end of the lead wire 461 is connected to the ground 469 via a switch 465.

With the above-described structure, when the charged aerosol particles flow into the FCAE 401, they are collected by the aerosol particle collector 450, so that electric charges are accumulated in the aerosol particle collector 450. Then, when the switch 465 is set to ON (is energized), the electric charges accumulated in the aerosol particle collector 450 move as a unit, and the ammeter 467 is capable of measuring a current equivalent to the total number of the electric charges. The calculation of the number of the aerosol particles will be further described later with reference to another drawing.

[Condensation Particle Counter (CPC)]

Next, the CPC 501 will be described.

Figure 8:
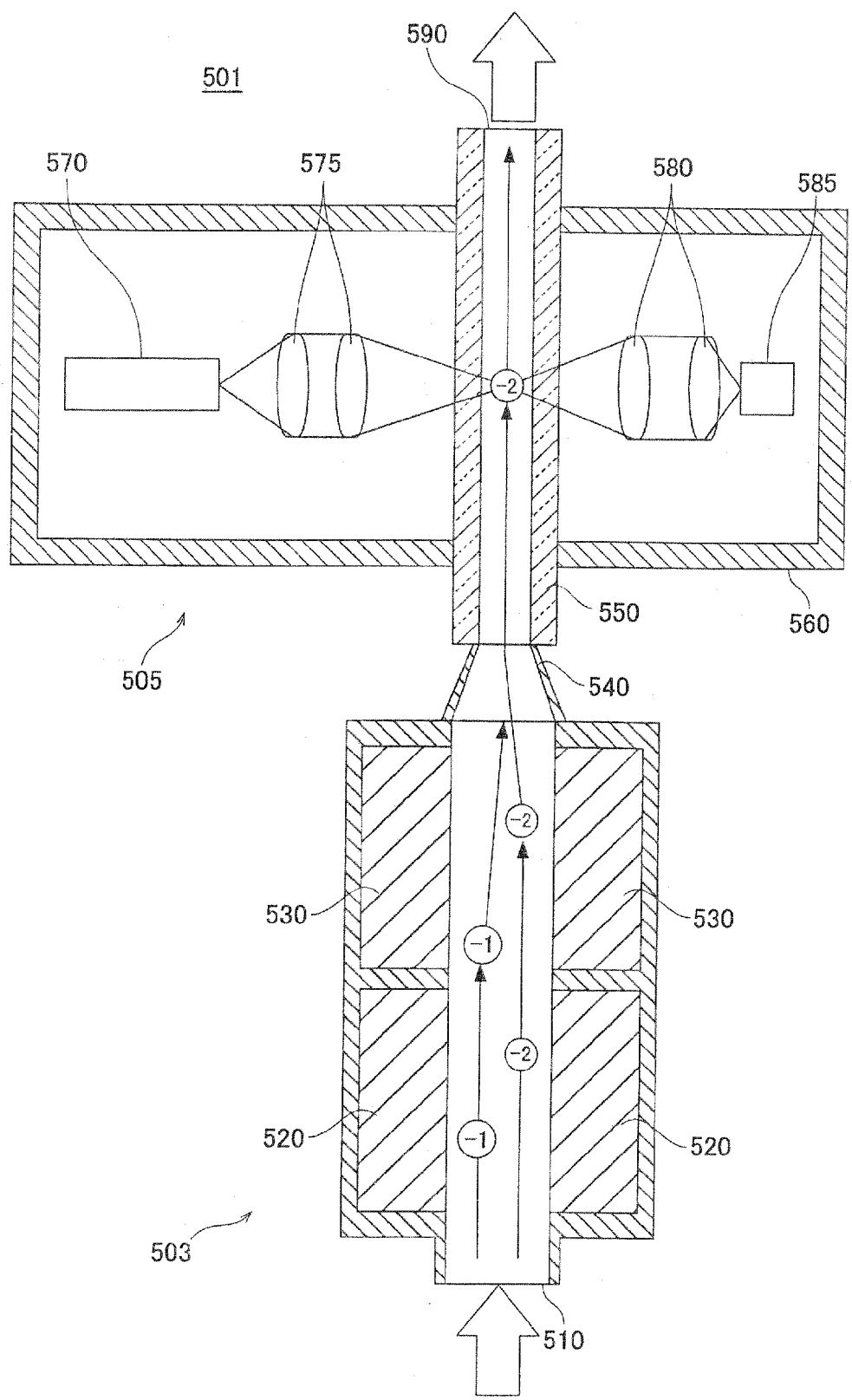
FIG. 8 is an explanatory diagram of a CPC.

As shown in FIG. 8, the CPC 501 includes: an aerosol particle condenser 503 which grows the aerosol particles large by condensation; and an aerosol particle optical detector 505 which detects the grown aerosol particles by an optical system.

The aerosol particles classified out and sent by the DMA 300 are made to flow into the aerosol particle condenser 503 from its inflow port 510. The aerosol particle condenser 503 is composed of a saturation part 520 and a condensing part 530. In the saturation part 520, alcohol or distilled water is diffused in a vapor form by being heated. Further, in the condensing part 530, gas that passes therein is cooled. Therefore, the aerosol particles flowing into the aerosol particle condenser 503 join the alcohol vapor or the water vapor in the saturation part 520 and both of them are sent to the condensing part 530. Then, in the condensing part 530, the condensation occurs with the aerosol particles serving as condensation nuclei, and they grow into large droplets owing to the alcohol vapor or the water vapor. The aerosol particles which are turned into the large droplets by the aerosol particle condenser 503 are sent to the aerosol particle optical detector 505 via a connection passage 540.

The aerosol particle optical detector 505 includes a flow cell 550, a light shielding vessel 560, a light emitting device 570, an irradiation optical lens system 575, a light-condensing optical lens system 580, and a light receiving device 585. The flow cell 550 is installed to penetrate through the light shielding vessel 560. Further, the light emitting device 570, the irradiation optical lens system 575, the light-condensing optical lens system 580, and the light receiving device 585 are installed in the light shielding vessel 560, and the light shielding vessel 560 has a structure so as not to allow light to enter its interior from the outside.

When scattered lights (reflected lights) from the aerosol particles flowing in the flow cell 550 are received, the aerosol particles are detected.

In the measurement of the aerosol particles classified out by the DMA 300, the FCAE 401 outputs, as a current, an accumulation value of the numbers of charges on the aerosol particles classified out per predetermined time. Further, the CPC 501 outputs a result equivalent to the number of the aerosol particles. Information on the result that is output is next transmitted to the measurement result analyzing device 600.

[Measurement Result Analyzing Device]

Next, in the measurement result analyzing device 600, the number of the aerosol particles is counted with respect to each particle size, based on the data measured by the FCAE 401 or the CPC 501. The measurement result analyzing device 600 includes an arithmetic operating function and a memory function, the process contents of the arithmetic operation are recorded in the memory function in advance, and the arithmetic operating function reads the process contents of its arithmetic operation as required, thereby counting the number of the aerosol particles with respect to each particle size from the data measured by the FCAE 401 or the CPC 501.

[Counting Result Outputting Device]

The counting result outputting device 700 displays the result of the counting of the aerosol particles, with respect to each particle size. For example, a display device (not shown) includes a display part for "Size (nm)" indicating a reference of the size of the aerosol particles and a display part for "Count" indicating the number (count value) of the counted aerosol particles corresponding to each particle size. The display part for "Size (nm)" displays a value of the reference particle size. The display part for "Count" displays the total number of the particles found from charging probability distribution, the number of particles with the reference particle size whose number of charges is 1, and the like. Further, they may be displayed as graphs. A display manner may be any as desired and is not limited to the example described here.

Incidentally, the counting result outputting device 700 may further include an external output terminal and may output data to another device through the terminal.

[Measurement of Aerosol Particles in Atmosphere]

In the measurement of the aerosol particles in the atmosphere, it is assumed that the aerosol particles whose particle size is larger than 100 nm are suspended in the atmosphere based on the inverse cubic size distribution law (Junge distribution), which is described when the particle density of the aerosol particles in the atmosphere is described by using FIG. 2.

Figure 10:
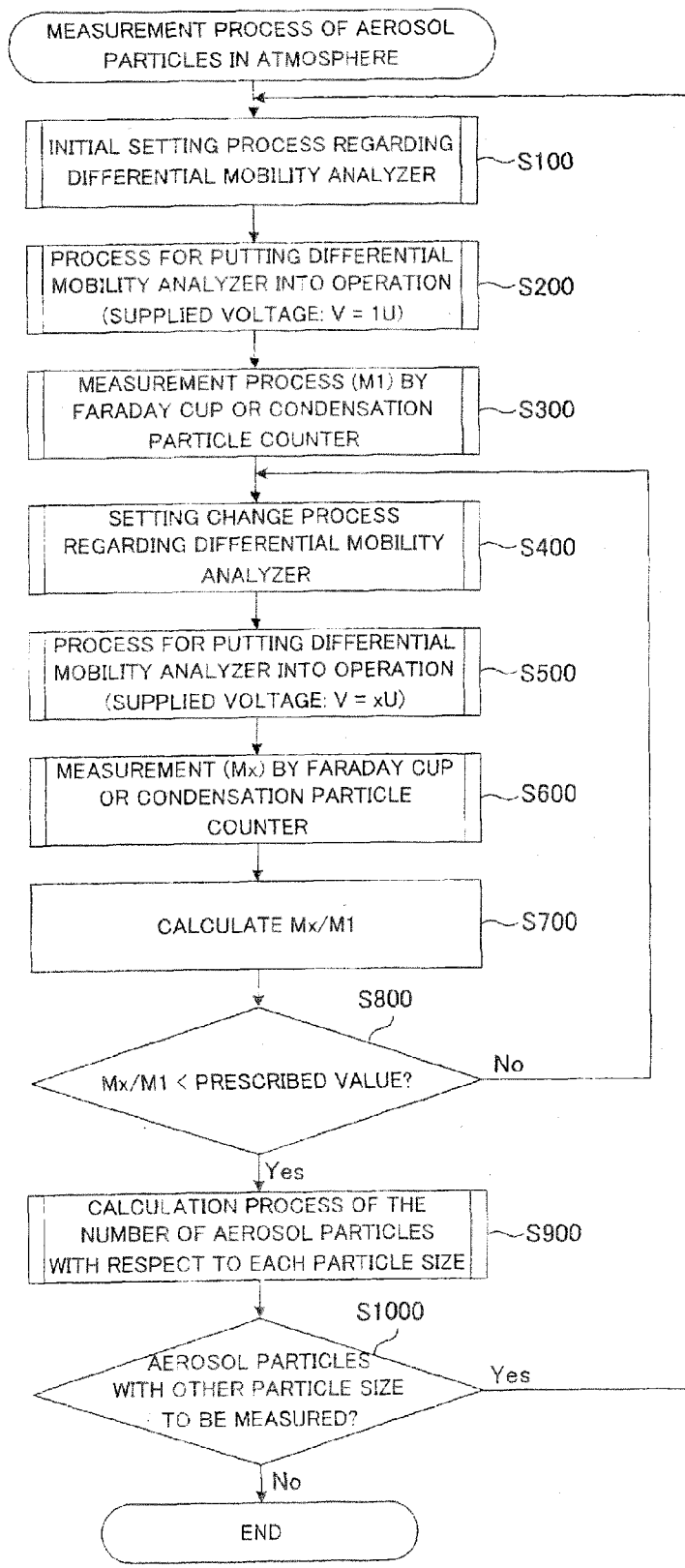
FIG. 10 is a flowchart showing a procedure example of a measurement process of the aerosol particles in the atmosphere.

FIG. 10 is a flowchart showing a measurement procedure of the aerosol particles in the atmosphere. Hereinafter, the contents will be described along the procedure example. Incidentally, the process in FIG. 10 may be executed by a control unit built in the particle size distribution measuring system 1.

Step S100: First, the particle size distribution measuring system 1 executes an initial setting process regarding the DMA 300. The concrete contents of the process will be further described later with reference to another flowchart.

[Initial Setting Process regarding DMA]

Figure 11:
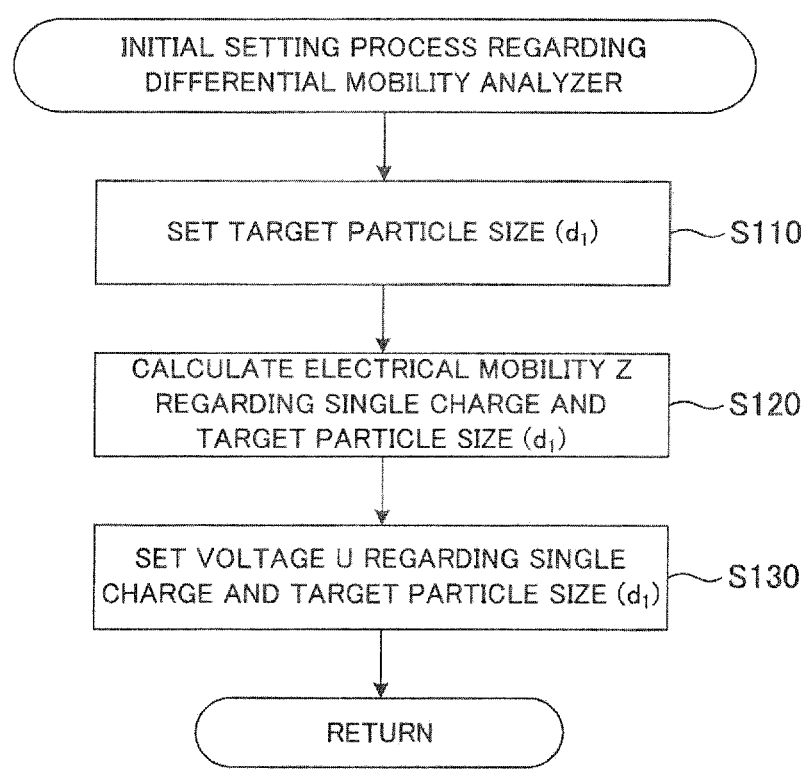
FIG. 11 is a flowchart showing a procedure example of an initial setting process regarding the DMA.

FIG. 11 is a flowchart showing a procedure example of the initial setting process regarding the DMA 300. Incidentally, the process in FIG. 11 may be executed by the control unit built in the particle size distribution measuring system 1.

Step S110: The particle size distribution measuring system 1 sets the particle size ($d_1$) as a measurement target. Concretely, the particle size distribution measuring system 1 sets the particle size ($d_1$) of the aerosol particles that are to be classified out by the DMA 300, on assumption that they are singly charged. The particle size distribution measuring system 1 next executes Step S120.

Step S120: The particle size distribution measuring system 1 executes the calculation of the electrical mobility Z regarding the target particle size ($d_1$) of the singly charged particles. Concretely, the particle size distribution measuring system 1 executes the calculation of the electrical mobility Z by using the above-described mathematical expression (1). The particle size distribution measuring system 1 next executes Step S130.

Step S130: The particle size distribution measuring system 1 sets the voltage U that is to be supplied to the DMA 300, as a voltage necessary for classifying out the singly charged aerosol particles with the target particle size ($d_1$). Concretely, the particle size distribution measuring system 1 calculates the voltage U that is to be supplied to the DMA 300, by using the electrical mobility Z calculated in the previous process Step S120 and the above-described mathematical expression (2).

Upon finishing the above-described procedure, the particle size distribution measuring system 1 returns to the measurement process (FIG. 10) of the aerosol particles in the atmosphere.

Step S200: Next, the particle size distribution measuring system 1 executes a process for putting the DMA 300 into operation. Concretely, the particle size distribution measuring system 1 supplied the voltage U calculated in the previous process Step S130 to the DMA 300 (supplied voltage V=1U) to put the DMA 300 into operation and classifies out the aerosol particles based on the electrical mobility $Z_1(U)$. The particle size distribution measuring system 1 next executes Step S300.

Step S300: The particle size distribution measuring system 1 executes the measurement (M1) by the FCAE 401 or the CPC 501. Here, the M1 represents the measurement result of the aerosol particles classified out based on the electrical mobility $Z_1(U)$. When the FCAE 401 or the CPC 501 finishes the measurement of the aerosol particles classified out based on the electrical mobility $Z_1(U)$, the particle size distribution measuring system 1 next executes Step S400.

Is Step S400: The particle size distribution measuring system 1 executes a setting change process regarding the DMA 300. The concrete contents of the process will be further described later with reference to another flowchart.

[Setting Change Process regarding DMA]

Figure 12:
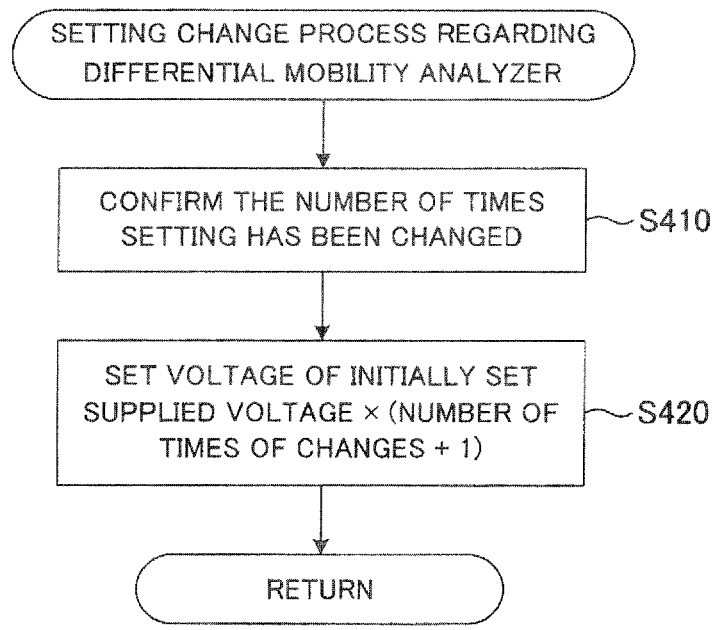
FIG. 12 is a flowchart showing a procedure example of a setting change process regarding the DMA.

FIG. 12 is a flowchart showing a procedure example of the setting change process regarding the DMA 300. Hereinafter, the contents will be described along the procedure example. Incidentally, the process in FIG. 12 may be executed by the control unit built in the particle size distribution measuring system 1.

Step S410: The particle size distribution measuring system 1 confirms the number of times the setting has been changed. Concretely, the particle size distribution measuring system 1 confirms the number of times the voltage V supplied to the DMA 300 has been changed. For example, when the voltage V set in the previous process is the initially set U, the number of times the setting has been changed corresponds to 1 indicating the first time. Besides, when the voltage V set in the previous process is 2U indicating the second time (or 3U indicating the third time), the number of times the setting has been changed is 2 (or 3) indicating the second time (or the third time). The particle size distribution measuring system 1 next executes Step S420.

Step S420: The particle size distribution measuring system 1 executes the setting for supplying the initially set supplied voltage (U)×(the number of times of the changes+1). For example, when the number of times of the changes confirmed in the previous process Step S410 is 1, the particle size distribution measuring system 1 sets the voltage that is to be supplied to the DMA 300 to 2U. Besides, when the number of times of the changes is 2 (or 3), the particle size distribution measuring system 1 sets the voltage that is to be supplied to the DMA 300 to 3U (or 4U).

Upon finishing the above-described procedure, the particle size distribution measuring system 1 returns to the measurement process (FIG. 10) of the aerosol particles in the atmosphere.

Step S500: The particle size distribution measuring system 1 executes a process for putting the DMA 300 into operation. Concretely, the particle size distribution measuring system 1 supplies the voltage 2U (or 3U, 4U) set in the previous process Step S420 to the DMA 300 (supplied voltage V=2U (or 3U, 4U)) to put the DMA 300 into operation and classifies out the aerosol particles based on the electrical mobility $Z_1(2U)$ (or $Z_1(3U)$, $Z_1(4U)$). The particle size distribution measuring system 1 next executes Step S600.

Step S600: The particle size distribution measuring system 1 executes a measurement Mx by the FCAE 401 or the CPC 501. The FCAE 401 or the CPC 501 outputs a measurement result Mx. Here, x represents any one of 2 to 4, M2 represents the measurement result of the aerosol particles classified out based on the electrical mobility $Z_1(2U)$, M3 represents the measurement result of the aerosol particles classified out based on the electrical mobility $Z_1(3U)$, and M4 represents the measurement result of the aerosol particles classified out based on the electrical mobility $Z_1(4U)$. When the measurement by the FCAE 401 is finished, the particle size distribution measuring system 1 next executes Step S700.

Step S700: From the measurement result M1 at the time of the initial setting and the measurement result Mx obtained when the setting is changed, the particle size distribution measuring system 1 calculates Mx/M1 being a ratio therebetween. Concretely, the particle size distribution measuring system 1 refers to the measurement result M1 obtained when, in the previous Step S300, the FCAE 401 or the CPC 501 measures the aerosol particles classified out based on the electrical mobility $Z_1(U)$. Further, the particle size distribution measuring system 1 refers to the measurement result M2 (or M3, M4) obtained when, in the previous process step S600, the FCAE 401 measures the aerosol particles classified out based on the electrical mobility $Z_1(2U)$ (or $Z_1(3U)$, $Z_1(4U)$). Then the particle size distribution measuring system 1 calculates Mx/M1. It is possible to calculate Mx/M1 by using the measurement result analyzing device 600.

Step S800: The particle size distribution measuring system 1 confirms whether or not re-measurement is required. It is possible to confirm this by using the measurement result analyzing device 600. Concretely, based on Mx/M1 calculated in the previous Step S700, the particle size distribution measuring system 1 confirms whether or not it is smaller than a prescribed value (for example, 0.01: 1%). If the prescribed value is set as approximately 1%, even disregarding the value of Mx/M1 causes no problem in observing the particle size distribution. It should be noted that the prescribed value is not limited to 1% and may be 0.1% and is appropriately adjustable. When confirming that Mx/M1 is smaller than the prescribed value (Yes), the particle size distribution measuring system 1 next executes Step S900. On the other hand, when Mx/M1 is not smaller than the prescribed value (No), the particle size distribution measuring system 1 next executes Step S400.

Step S900: The particle size distribution measuring system 1 calculates the number of the aerosol particles ($d_1$) classified out by the DMA 300. It is possible to calculate this by using the measurement result analyzing device 600. Here, a description will be given of a case where M2/M1 and M3/M1 are not smaller than the prescribed value (1%) and M4/M1 is smaller than the prescribed value (1%). A description of other cases will be skipped because the calculation is possible as required based on the calculation method using the following mathematical expressions.

Note that the measurement results M1, M2, M3, M4 measured by the FCAE 401 are current-equivalent and $M_{FCAE}(Z_1(U))$ is quantity-equivalent. On the other hand, the measurement results M1, M2, M3, M4 measured by the CPC 501 are quantity-equivalent and $M_{CPC}(Z_1(U))$ is similarly quantity-equivalent.

Here, a distribution function of the charged aerosols particles corresponding to each particle size, actually classified out by the DMA 300 based on the electrical mobility $Z_1(U)$ is defined as follows. The distribution function of singly charged aerosol particles corresponding to the particle size $d_1$ is defined as $C_1(Z_1(U))$, the distribution function of doubly charged aerosol particles corresponding to the particle size $d_2$ is defined as $C_2(Z_1(U))$, the distribution function of triply charged aerosol particles corresponding to the particle size $d_3$ is defined as $C_3(Z_1(U))$, and the distribution function of four-fold charged aerosol particles corresponding to the particle size $d_4$ is defined as $C_4(Z_1(U))$. Note that the distribution function expresses the quantity of the relevant particles. For example, $C_1(Z_1(U))$ expresses the quantity of the singly charged particles corresponding to the electrical mobility $Z_1(U)$.

Therefore, the measurement result measured by the FCAE 401 or the CPC 501 is expressed by the following mathematical expression (3) or mathematical expression (4) when the aforesaid distribution function of the aerosol particles is used.

$$M_{FCAE}(Z_1(U)) = \eta_{FCAE}(Z_1(U)) \cdot \sum_{p=1}^{4} p \cdot C_p(Z_1(U)) \tag{3}$$

Here, $M_{FCAE}(Z_1(U))$ represents the quantity obtained from the measurement result by the FCAE 401 for the aerosol particles classified out based on $Z_1(U)$, $\eta_{FCAE}(Z_1(U))$ represents detection efficiency of the FCAE 401 for the aerosol particles classified out based on $Z_1(U)$, and p represents the number of charges. Note that $\eta_{FCAE}(Z_1(U))$ is generally 1 (concretely, 0.99999). Further, detection efficiency is also 1 in the other $\eta_{FCAE}Z_1(2U), \eta_{FCAE}Z_1(3U), \ldots \eta_{FCAE}Z_1(pU)$.

$$M_{CPC}(Z_1(U)) = \sum_{p=1}^{4} \eta_{CPC}(Z_1(pU)) \cdot C_p(Z_1(U)) \tag{4}$$

Here, $M_{CPC}(Z_1(U))$ represents the quantity obtained from the measurement result by the CPC 501 for the aerosol particles classified out based on $Z_1(U)$, $\eta_{CPC}(Z_1(pU))$ represents detection efficiency of the CPC 501 for the aerosol particles classified out based on $Z_1(pU)$, and p represents the number of charges. Therefore, the mathematical expression (4) indicates that the detection efficiency $\eta_{CPC}$ differs depending on p representing the number of charges. Note that a calibrated value of the CPC 501 means this detection efficiency $\eta_{CPC}$.

Incidentally, as described by using FIG. 6 above, since the aerosol particles classified out by the DMA 300 based on the electrical mobilities $Z(U)$ to $Z(4U)$ also include multiply charged ones, they are also included in the measurement results M1 to M4 by the FCAE 401 or the CPC 501.

Figure 9:
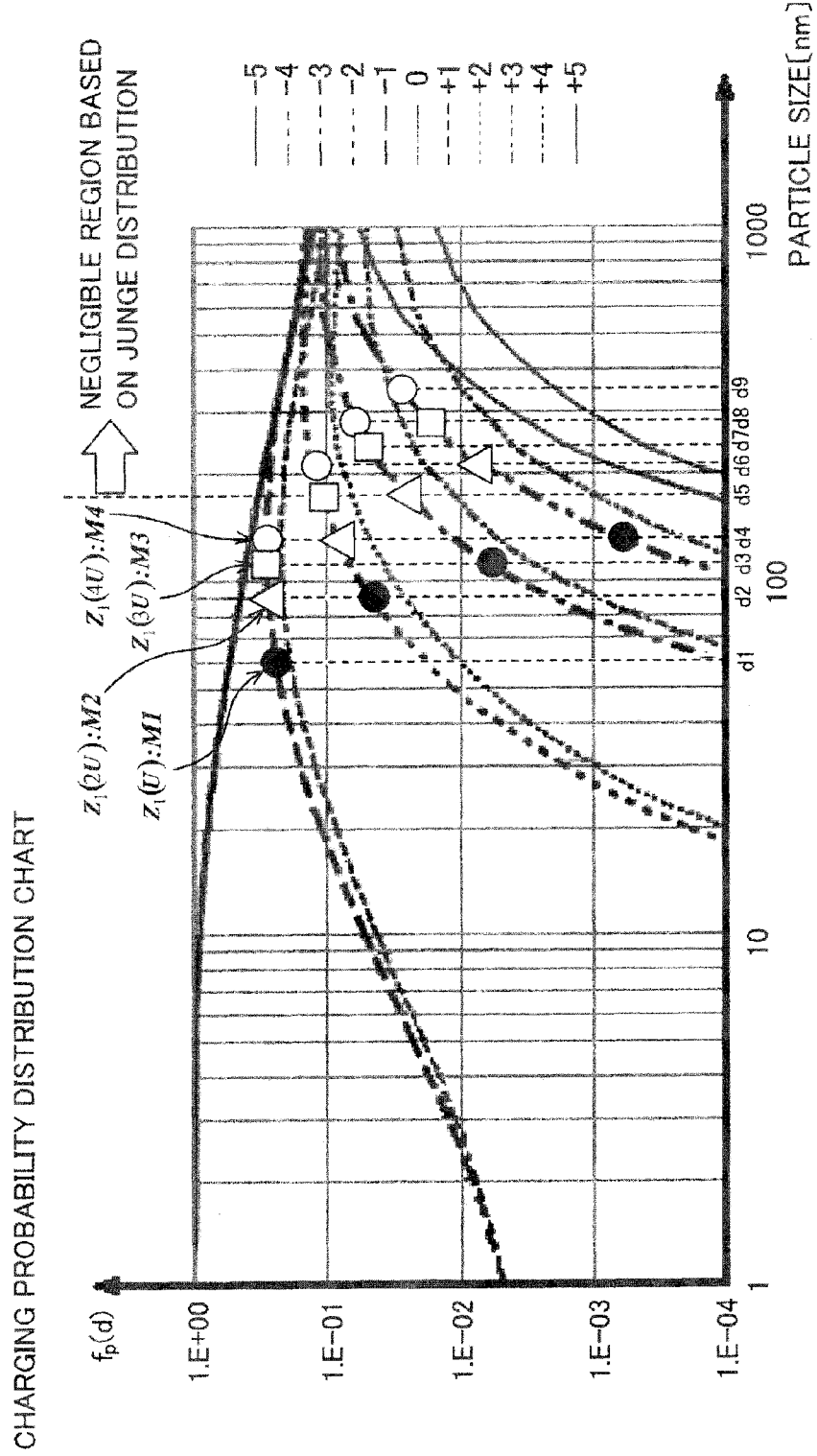
FIG. 9 is an explanatory chart of charging probability distribution obtained when measurement results M1 to M4 corresponding to the particle size of and the number of charges on the aerosol particles are plotted.

FIG. 9 is a chart where the aerosol particles classified out by the DMA 300 based on the electrical mobilities $Z(U)$ to $Z(4U)$ are plotted in the charging probability distribution chart (FIG. 4) in correspondence to the particle size and the number of charges. Concretely, the charging probability of the singly charged aerosol particles with the particle size $d_4$ classified out based on the electrical mobility $Z_1(4U)$ (○) is 30%, and the charging probability of doubly charged aerosol particles with the particle size $d_5$ classified out based on the electrical mobility $Z_1(3U)$ (□) is approximately 10%. For example, if the number of the singly charged aerosol particles with the particle size $d_4$ classified out based on the electrical mobility $Z_1(4U)$ (○) is negligibly small, the doubly charged aerosol particles whose particle size is $d_5$ larger than $d_4$ and which are classified out based on the electrical mobility $Z_1(3U)$ (□) and the doubly charged aerosol particles with a large number of charges and with the particle size $d_4$ classified out based on the electrical mobility $Z_1(2U)$ (△) are also negligible.

Further, a function expressing the charging probability is defined as $f_p(Z_1(nU))$. A relationship among the distribution functions of aerosol particles corresponding to the respective numbers of charges, classified out based on the different electrical mobilities Z is expressed by the following mathematical expressions (5). Here, p represents the number of charges and nU represents the supplied voltage. For example, among aerosol particles with the particle size $d_4$ in the charged equilibrium state classified out based on the electrical mobility $Z_1(4U)$, the charging probability function of the singly charged aerosol particles with the particle size $d_4$ (○) is expressed as $f_1(Z_1(4U))$, and the charging probability function of the fourfold charged aerosol particles with the particle size $d_4$ is expressed as $f_4(Z_1(4U))$. Here, the fourfold charged aerosol particles with the particle size $d_4$ classified out based on the electrical mobility $Z_1(U)$ (●) correspond to this charging probability function $f_4(Z_1(4U))$. Further, by dividing the distribution function $C_1(Z_1(4U))$ for the singly charged aerosol particles with the particle size $d_4$ classified out based on the electrical mobility $Z_1(4U)$ by the charging probability function $f_1(Z_1(4U))$, it is possible to find the total number of particles with the particle size $d_4$, and by integrating this total number of particles and the charging probability function $f_4(Z_1(4U))$ for aerosol particles with the particle size $d_4$ to have the fourfold charge, it is possible to find the number of fourfold charged particles $C_4(Z_1(U))$ with the particle size $d_4$ classified out based on the electrical mobility $Z_1(U)$.

$$C_2(Z_1(U)) = \frac{f_2(2U)}{f_1(Z(2U))} \cdot C_1(Z_1(2U)), \quad (5)$$

$$C_2(Z_1(2U)) = \frac{f_2(Z_1(4U))}{f_1(Z_1(4U))} \cdot C_1(Z_1(4U))$$

$$C_3(Z_1(U)) = \frac{f_3(Z_1(3U))}{f_1(Z_1(3U))} \cdot C_1(Z_1(3U))$$

$$C_4(Z_1(U)) = \frac{f_4(Z_1(4U))}{f_1(Z_1(4U))} \cdot C_1(Z_1(4U))$$

Here, if the case where M2/M1 and M3/M1 are not smaller than the prescribed value (1%) and M4/M1 is smaller than the prescribed value is supplied to the above, since the measurement result M4 of the aerosol particles classified based on the electrical mobility $Z_1(4U)$ is negligibly small, $C_1(Z_1(4U))=0$. Similarly, $C_4(Z_1(U))=C_2(Z_1(2U))=0$.

$M_{FCAE}(Z_1(U))$ to $M_{FCAE}(Z_1(4U))$ obtained from the result when the FCAE 401 measures the aerosol particles classified out based on the electrical mobilities $Z_1(U)$ to $Z_1(4U)$ can be expressed by a mathematical expression (6) to a mathematical expression (8), considering that $M_{FCAE}(Z_1(4U))=C_1(Z_1(4U))=0$. In this manner, the singly to triply charged particles are classified out based on the electrical mobility $Z_1(U)$, and the singly charged particles are classified out based on the electrical mobilities $Z_1(2U)$ and $Z_1(3U)$.

$$M_{FCAE}(Z_1(U)) = \eta_{FCAE}(Z_1(U)) \cdot C_1(Z_1(U)) + \eta_{FCAE}(Z_1(U)) \cdot 2 \cdot C_2(Z_1(U)) + \eta_{FCAE}(Z_1(U)) \cdot 3 \cdot C_3(Z_1(U)) \quad (6)$$

$$M_{FCAE}(Z_1(2U)) = \eta_{FCAE}(Z_1(U)) \cdot C_1(Z_1(2U)) \quad (7)$$

$$M_{FCAE}(Z_1(3U)) = \eta_{FCAE}(Z_1(U)) \cdot C_1(Z_1(3U)) \quad (8)$$

Further, from the above mathematical expression (5), mathematical expression (6), mathematical expression (7), and mathematical expression (8), the following mathematical expression (9) can be derived.

$$\eta_{FCAE}(Z_1(U)) \cdot C_1(Z_1(U)) = M_{FCAE}(Z_1(U)) - \quad (9)$$
$$2 \cdot \frac{f_2(Z_1(2U))}{f_1(Z_1(2U))} \cdot M_{FCAE}(Z_1(2U)) - 3 \cdot \frac{f_3(Z_1(3U))}{f_1(Z_1(3U))} \cdot M_{FCAE}(Z_1(3U))$$

Since only the singly charged particles are classified out based on the electrical mobilities $Z_1(2U)$ and $Z_1(3U)$, it is possible to find $M_{FCAE}(Z_1(2U))$ and $M_{FCAE}(Z_1(3U))$ from the measurement by the FCAE 401. Then, $C_1(Z_1(2U))$ is found from the mathematical expression (7), whereby $C_2(Z_1(U))$ can be found from the mathematical expression (5). Further, $C_1(Z_1(3U))$ is found from the mathematical expression (8), whereby $C_3(Z_1(U))$ can be found from the mathematical expression (5). Therefore, the numbers of the doubly and triply charged particles classified out based on the electrical mobility $Z_1(U)$ are found, so that the number of singly charged particles $\eta_{FCAE}(Z_1(U)) \cdot C_1(Z_1(U))$ can be found by using the measurement result $M_{FCAE}(Z_1(U))$.

Further, by the same calculation method, the following mathematical expression (10) can be derived for the CPC 501.

$$\eta_{CPC}(Z_1(U)) \cdot C_1(Z_1(U)) = M_{CPC}(Z_1(U)) - \quad (10)$$
$$\frac{f_2(Z_1(2U))}{f_1(Z_1(2U))} \cdot M_{CPC}(Z_1(2U)) - \frac{f_3(Z_1(3U))}{f_1(Z_1(3U))} \cdot M_{CPC}(Z_1(3U))$$

As described above, when M4/M1 is smaller than 1%, it is possible to measure the number of the aerosol particles classified out by the DMA 300 based on the electrical mobility $Z_1(U)$. The FCAE 401 or the CPC 501 measures the aerosol particles classified out based on a given electrical mobility Z, and it is possible to count the number of the aerosol particles based on the measurement results $M_{FCAE}$, $M_{CPC}$ and a charging probability ratio of the charging probability functions.

As for the particle size distribution of the aerosol particles in the atmosphere, the density with respect to each particle size follows the Junge distribution, which indicates that, as for the aerosol particles whose particle size is larger than 100 nm, because the number thereof is extremely small based on the inverse cubic size distribution law, and because the measurement is based on the charging probability distribution of the aerosol particles, it almost suffices if fourfold to sixfold charged ones are measured.

When the number of the aerosol particles is counted with respect to each particle size from the measurement results M1, M2, M3, M4 in the current calculation process Step S900, the particle size distribution measuring system 1 next executes Step S1000.

Step S1000: The particle size distribution measuring system 1 confirms whether or not to measure the aerosol particles with another particle size. When it is confirmed that the aerosol particles with another particle size are to be measured (Yes), the particle size distribution measuring system 1 next executes Step S100. On the other hand, when the aerosol particles with another particle size are not to be measured (No), the particle size distribution measuring system 1 finishes the measurement of the aerosol particles in the atmosphere.

[Calibration of CPC 501]

Next, calibration of the CPC 501 will be described. The CPC 501 is a device, as described above, which condenses fine aerosol particles to grow them into large droplets and thereafter optically detects the droplets. The calibration is necessary when the aerosol particles are counted by the CPC 501. For the calibration of the CPC 501, the aerosol particle generating device 100 capable of generating aerosol particles with an intended particle size distribution for each particle size is used. For example, as the aerosol particles for the calibration, polystyrene latex (PSL) particles high in sphericity and having a uniform particle size may be used, or soot generated in large volume by a carbon cluster synthesizing device may be used. Incidentally, it is known that the density distribution of the soot with respect to each particle size also has the same behavior as that of the aforesaid Junge distribution (the density of particles whose particle size is 100 nm or more is based on the inverse cubic size distribution law).

Figure 13:
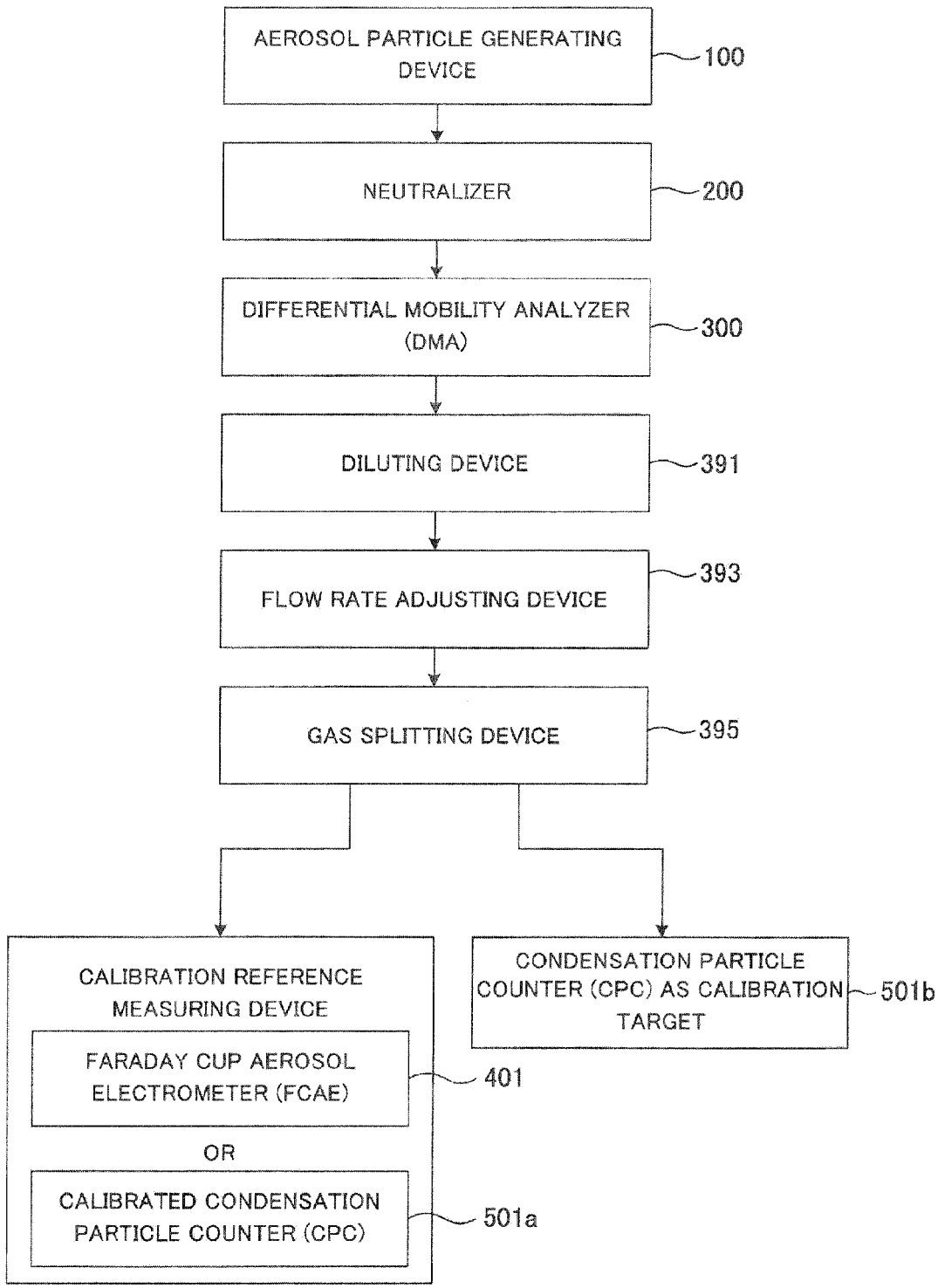
FIG. 13 is an explanatory diagram of a structure example, showing a relation between a CPC being a calibration target and a measuring device which measures data serving as a reference of the calibration.

FIG. 13 is an explanatory diagram of a structure example, showing a relationship between a CPC being a calibration target and a measuring device which measures data used as a reference of the calibration.

As shown in FIG. 13, the relationship between the CPC being the calibration target and the device for measuring the reference of the calibration is configured of the aerosol particle generating device 100, the neutralizer 200, the DMA 300, a diluting device 391, a flow rate adjusting device 393, a gas splitting device 395, a calibration reference measuring device (the FCAE 401, or a calibrated CPC 501a), and a CPC 501b being the calibration target.

The aerosol particles generated by the aerosol particle generating device 100 are sent to the DMA 300 after being charged by the neutralizer 200. Then, gas containing the aerosol particles classified out by the DMA 300 is sent to the diluting device 391. In the diluting device 391, the gas is diluted to an appropriate concentration and is thereafter sent to the flow rate adjusting device 393. In the flow rate adjusting device 393, the gas is adjusted in its flow rate and is thereafter sent to the gas splitting device 395. The gas splitting device 395 is a device which splits the sent gas containing the aerosol particles to send the gas to the calibration reference measuring device (the FCAE 401 or the calibrated CPC 501a) and to the CPC 501b being the calibration target. For example, 50% of the gas sent to the gas splitting device 395 is sent to each of the calibration reference measuring device (the FCAE 401 or the calibrated CPC 501a) and the CPC 501b being the calibration target.

[Calibration Process of CPC]

In the calibration process of the CPC 501b, the measurement result serving as the reference of the calibration, which is measured by the calibration reference measuring device (the FCAE 401 or the calibrated CPC 501a) described above and the measurement result measured by the CPC 501b being the calibration target are compared for the calibration. Processes before the calculation of the measurement result in each of them are the same as those of the above-described measurement process (FIG. 10) of the aerosol particles in the atmosphere, and therefore a description thereof will be skipped. Here, a case where M2/M1 is smaller than 1% and a case where M4/M1 is smaller than 1% will be described.

[Case where M2/M1 is Smaller than 1%]

First, the case where a ratio of the measurement result M1 and the measurement result M2 which are obtained when the FCAE 401 measures the aerosol particles classified out based on the electrical mobility $Z(U)$ and based on the electrical mobility $Z(2U)$ respectively is smaller than 1% will be described.

Based on the initial electrical mobility and the mathematical expression (3), the measurement results by the FCAE 401 are expressed by the following mathematical expression (11) and mathematical expression (12).

$$M_{FCAE}(Z_1(U)) = \eta_{FCAE}(Z_1(U)) \cdot C_1(Z_1(U)) + \eta_{FCAE}(Z_1(U)) \cdot 2 \cdot C_2(Z_1(U)) + \ldots \quad (11)$$

$$M_{FCAE}(Z_1(2U)) = \eta_{FCAE}(Z_1(2U)) \cdot C_1(Z_1(2U)) \quad (12)$$

Here, based on the charging probability distribution chart (ISO 15900:2009) described in FIG. 4, the function expressing the charging probability is defined as $f_p(Z_1(nU))$. Here p represents the number of charges and nU represents a supplied voltage.

Therefore, a relationship between the distribution functions $C_2(Z_1(U))$, $C_1(Z_1(2U))$ of the doubly charged aerosol particles classified out based on the electrical mobility $Z(U)$ and the singly charged aerosol particles classified out based on the electrical mobility $Z(2U)$ is expressed by the following mathematical expression (13).

$$C_2(Z_1(U)) = \frac{f_2(Z_1(2U))}{f_1(Z_1(2U))} \cdot C_1(Z_1(2U)) \quad (13)$$

Here, because M2/M1 is smaller than 1%, $(M_{FCAE}(Z_1(2U))/M_{FCAE}(Z_1(U))) \leq 0.01$, and $C_1(Z_1(2U))$ in the mathematical expression (12) is negligibly small, it is possible to derive $C_2(Z_1(U))=0$ in the mathematical expression (11).

Therefore, the above mathematical expression (11) can be expressed by the following mathematical expression (14).

$$M_{FCAE}(Z_1(U)) = \eta_{FCAE}(Z_1(U)) \cdot C_1(Z_1(U)) \quad (14)$$

Meanwhile, from the mathematical expression (4), the measurement result by the CPC 501b can be expressed by the following expression (15).

$$M_{CPC}(Z_1(U)) = \eta_{CPC}(Z_1(U)) \cdot C_1(Z_1(U)) \quad (15)$$

Therefore, the detection efficiency $\eta_{CPC}(Z_1(U))$ of the CPC 501 is expressed by the following mathematical expression (16) from the above mathematical expression (14) and mathematical expression (15).

$$\eta_{CPC}(Z_1(U)) = \frac{M_{CPC}(Z_1(U))}{M_{FCAE}(Z_1(U))} \cdot \eta_{FCAE}(Z_1(U)) \quad (16)$$

In the above, it is described that, when M2/M1 is smaller than 1%, the detection efficiency $\eta_{CPC}(Z_1(U))$ in the measurement of the aerosol particles classified out by the DMA 300 based on the electrical mobility $Z_1(U)$ is expressed by the mathematical expression (16). For example, when $M_{FCAE}(Z_1(U))$ is 10000 and $M_{CPC}(Z_1(U))$ is 7000, $\eta_{CPC}(Z_1(U))$ is calculated as 0.7. Therefore, as a calibrated value of the CPC 501b corresponding to the electrical mobility $Z_1(U)$, $\eta_{CPC}(Z_1(U))=0.7$ is employed.

Here, as the calibrated value of the CPC 501b, $\eta_{CPC}(Z_1(U))$ may be calculated, with the measurement result $M_{FCAE}(Z_1(U))$ and the detection efficiency $\eta_{FCAE}(Z_1(U))$ by the FCAE 401 being replaced by the measurement result $M_{CPCa}(Z_1(U))$ and the detection efficiency $\eta_{CPCa}(Z_1(U))$ by the calibrated CPC 501a respectively.

[Case where M4/M1 is Smaller than 1%]

Next, a description will be given of the case where the ratio of the measurement result M1 and the measurement result M4 which are obtained when the FCAE 401 measures the aerosol particles classified out based on the electrical mobility Z(U) and the electrical mobility Z(4U) respectively is smaller than 1%. Concretely, the case where M2/M1 is smaller than 1% is described above, and next, the case where M2/M1 and M3/M1 are not smaller than 1% and M4/M1 is smaller than 1% will be described.

As described above in the measurement process of the aerosol particles in the atmosphere, the measurement result by the FCAE 401 is expressed by the mathematical expression (6), the mathematical expression (7), and the mathematical expression (8). Further, $C_1(Z_1(2U))$ is found from the mathematical expression (7), and $C_2(Z_1(U))$ is found from the aforesaid mathematical expression (5). Further, it is described that $C_1(Z_1(3U))$ is found from the mathematical expression (8), whereby a $C_3(Z_1(U))$ can be found from the aforesaid mathematical expression (5). It is described that, since the numbers of doubly and triply charged particles classified out based on the electrical mobility ($Z_1(U)$) are found, it is possible to find the number of singly charged particles $\eta_{FCAE}(Z_1(U)) \cdot C_1(Z_1(U))$ by using the measurement result $M_{FCAE}(Z_1(U))$. Then, it is described that by the similar calculation method, it is possible to derive the mathematical expression (10) for the CPC 501.

Therefore, the detection efficiency $\eta_{CPC}(Z_1(U))$ of the CPC 501 is expressed as the following mathematical expression (17) from the aforesaid mathematical expression (9) and mathematical expression (10).

$$\eta_{CPC}(Z_1(U)) = \frac{M_{CPC}(Z_1(U)) - \sum_{p=2}^{3} \alpha_p \cdot M_{CPC}(Z_1(pU))}{M_{FCAE}(Z_1(U)) - \sum_{p=2}^{3} p \cdot \alpha_p \cdot M_{FCAE}(Z_1(pU))} \cdot \eta_{FCAE}(Z_1(U)) \quad (17)$$

Here, $\alpha p$ represents a charging probability ratio corresponding to the number of charges, and concretely, $\alpha_2 = f_2(Z_1(2U))/f_1(Z_1(2U))$, and $\alpha_3 = f_3(Z_1(3U))/f_1(Z_1(3U))$.

In the above, it is described that, when M4/M1 is smaller than 1%, the detection efficiency $\eta_{CPC}(Z_1(U))$ in the measurement of the aerosol particles classified out by the DMA 300 based on the electrical mobility $Z_1(U)$ is expressed by the mathematical expression (17).

In the above, the description is given of the case where M2/M1 and M4/M1 are smaller than 1%, but in other cases, it is also possible to similarly derive the detection efficiency $\eta_{CPC}(Z_1(U))$, and a general solution of the is detection efficiency of the CPC 501 is expressed by the following expression (18).

$$\eta_{CPC}(d_1) = \eta_{CPC}(Z_1(U)) = \frac{M_{CPC}(Z_1(U)) - \sum_{p \geq 2}^{n} \alpha_p \cdot M_{CPC}(Z_1(pU))}{M_{FCAE}(Z_1(U)) - \sum_{p \geq 2}^{n} p \cdot \alpha_p \cdot M_{FCAE}(Z_1(pU))} \cdot \eta_{FCAE}(Z_1(U)) \quad (18)$$

Here, $d_1$ represents the particle size of the aerosol particles for the calibration of the CPC 501. Further, the charging probability ratio $\alpha_p$ corresponding to the number of charges p is shown in FIG. 14.

As described above, the aerosol particles classified out based on a given electrical mobility Z are measured by the FCAE 401 and the CPC 501, and the detection efficiency $\eta_{CPC}$ of the CPC 501 is calculated based on the measurement results $M_{FCAE}$, $M_{CPC}$ and the charging probability ratio of the charging probability functions. Then, by employing the calculated detection efficiency $\eta_{CPC}$ as the calibrated value, it is possible to count the number of particles also in the CPC 501.

As described above, the aerosol particles are generated by the aerosol particle generating device 100, the aerosol particles are classified by the neutralizer 200 and the DMA 300, and thereafter the aerosol particles made to flow by the gas splitting device 395 in a predetermined amount per each are measured by the FCAE 401 and the CPC 501 being the calibration target. Then, based on the measurement results $M_{FCAE}$, $M_{CPC}$ and the charging probability ratio of the charging probability functions, the detection efficiency $\eta_{CPC}$ of the CPC 501 is calculated, and by employing the calculated $\eta_{CPC}$ as the calibrated value, it is possible to count the number of the aerosol particles also in the CPC 501.

What is claimed is:
1. A particle size distribution measuring system comprising:
   a neutralizer which puts aerosol particles into a charged equilibrium state;
   a DMA (Differential Mobility Analyzer) which classifies the aerosol particles charged by the neutralizer in a predetermined electric field based on electrical mobility and which, in a state where a reference voltage supplied to form the electric field is initially set to a voltage value U, executes the first classifying of the aerosol particles under the supplied voltage having the initially set voltage value U;
   an aerosol particle measuring device which measures the aerosol particles classified out by the DMA, by an electrical and/or optical measuring method and outputs a result of the measurement; and
   a measurement result analyzing device which confirms whether or not a predetermined condition is satisfied, based on the measurement result output by the aerosol particle measuring device, and when confirming that the condition is satisfied, calculates particle size distribution with respect to each particle size from the measurement result output by the aerosol particle measuring device, and when confirming that the condition is not satisfied, executes:
   (a) causing the DMA, in a state where the voltage supplied to form the electric field is re-set to a sum of the voltage value of the voltage supplied in the previous classifying (previous value) and the voltage value U, to execute re-classifying of the aerosol particles under the supplied voltage having the re-set voltage value;

(b) causing the aerosol particle measuring device
(b-1) to output a first measurement result M1 which is the measurement result of the aerosol particles that the DMA classifies out under the supplied voltage having the initially set voltage value U, and
(b-2) to output a new measurement result Mx which is the re-measurement result of the aerosol particles that are classified out, every time the re-classifying is executed in the (a) by the DMA;
(c) calculating a ratio of the measurement result Mx, which the aerosol particle measuring device is caused to output in the (b-2), to the measurement result M1, which the aerosol particle measuring device is caused to output in the (b-1);
(d) confirming that the condition is not satisfied yet when the ratio calculated in the (c) is larger than a prescribed value, to execute the (a), (b), and (c), while confirming that the condition is satisfied when the ratio calculated in the (c) is equal to or smaller than the prescribed value; and
(e) when confirming that the condition is satisfied, calculating the particle size distribution with respect to each particle size from the measurement result based on a charging probability for the aerosol particles to be charged by the neutralizer.

2. The particle size distribution measuring system according to claim 1, further comprising
an aerosol particle collecting device which collects the aerosol particles with a plurality of kinds of particle sizes suspended in the atmosphere and makes the collected aerosol particles flow in the neutralizer,
wherein the DMA sets particle size groups as measurement targets among the plural kinds of particle sizes in a plurality of manners, and calculates the reference voltage value U for each of the set particle size groups, to initially set the calculated voltage values U as the reference voltage in sequence.

3. The particle size distribution measuring system according to claim 1,
wherein the aerosol particle measuring device includes:
a Faraday cup aerosol electrometer (FCAE) which electrically measures the aerosol particles classified out by the DMA by collecting electric charges on the aerosol particles;
a condensation particle counter (CPC) which grows the aerosol particles classified out by the DMA large by means of condensation, irradiates the grown aerosol particles with a laser beam, and optically measures the aerosol particles by receiving scattered lights from the irradiated aerosol particles; and
a splitting device which splits the aerosol particles classified out by the DMA to send the split aerosol particles to the FCAE and the CPC, and
wherein the aerosol particle measuring device calibrates the CPC by comparing the particle size distribution which is calculated by the measurement result analyzing device based on a result of the measurement by the FCAE and the particle size distribution which is calculated by the measurement result analyzing device based on a result of the measurement by the CPC.

4. The particle size distribution measuring system according to claim 3,
wherein, for the calibration, the aerosol particle measuring device calculates detection efficiency regarding the optical measurement by the CPC based on the following relational expression (18):

$$\eta_{CPC}(d_1) = \eta_{CPC}(Z_1(U)) = \frac{M_{CPC}(Z_1(U)) - \sum_{p \geq 2}^{n} \alpha_p \cdot M_{CPC}(Z_1(pU))}{M_{FCAE}(Z_1(U)) - \sum_{p \geq 2}^{n} p \cdot \alpha_p \cdot M_{FCAE}(Z_1(pU))} \cdot \eta_{FCAE}(Z_1(U)) \quad (18)$$

where
$\eta_{CPC}(Z_1(U))$ is the detection efficiency regarding the optical measurement by the CPC,
$\eta_{FCAE}(Z_1((U))$ is detection efficiency regarding the electrical measurement by the FCAE,
p is a value regarding the number of times the measurement is executed by the aerosol particle measuring device,
$\alpha_p$ is a value regarding a charging probability for the aerosol particles to be charged by the neutralizer and regarding the p.
$M_{cpc}(Z_1(U))$ is the first measurement result output by the aerosol particle measuring device based on the measurement result by the CPC,
$M_{cpc}(Z_1(pU))$ is the new measurement result, corresponding to the p, output again by the aerosol particle measuring device based on the measurement result by the CPC,
$M_{FCAE}(Z_1(U))$ is the first measurement result output by the aerosol particle measuring device based on the measurement result by the FCAE, and
$M_{FCAE}(Z_1(pU))$ is the new measurement result, corresponding to the p, output again by the aerosol particle measuring device based on the measurement result by the FCAE.

5. A particle size distribution measuring method comprising:
(A) a step of putting aerosol particles into a charged equilibrium state;
(B) a step of classifying the aerosol particles charged in the step (A), in a predetermined electric field based on electrical mobility, the step being a step of initially setting a reference voltage supplied to form the electric field to a voltage value U, and executing the first classifying of the aerosol particles under the supplied voltage having the initially set voltage value U;
(C) a step of measuring the aerosol particles classified out in the step (B), by an electrical or/and optical measuring method and outputting a result of the measurement;
(D) a step of confirming whether or not a predetermined condition is satisfied, based on the measurement result output in the step (C); and
(E) a step of, when confirming in the step (D) that the condition is satisfied, calculating particle size distribution with respect to each particle size from the measurement result output in the step (C), and when confirming that the aforesaid condition is not satisfied, executing:
(a) a procedure to re-set the voltage supplied to form the electric field to a sum of the voltage value of the voltage supplied in the previous classifying executed in the step (B) (previous value) and the voltage value U, and execute re-classifying of the aerosol particles under the supplied voltage having the re-set voltage value;
(b-1) a procedure to output a first measurement result M1 which is the measurement result of the aerosol particles that are classified out in the step (B) under the supplied voltage having the initially set voltage value U, and
(b-2) a procedure to output a new measurement result Mx which is the re-measurement result of the aerosol particles that are classified out, every time the re-classifying is executed in the procedure (a);
(c) a procedure to calculate a ratio of the measurement result Mx, which is output in the procedure (b-2), to the measurement result M1, which is output in the procedure (b-1); and
(d) a procedure to confirm that the condition is not satisfied yet when the ratio calculated in the procedure (c) is larger than a prescribed value, to execute the procedures (a), (b), and (c), while confirming that the condition is satisfied when the ratio calculated in the procedure (c) is equal to or smaller than the prescribed value; and
(e) a procedure to, when confirming that the condition is satisfied, calculate the particle size distribution with respect to each particle size from the measurement result based on a charging probability for the aerosol particles to be charged in the step (A).

6. The method according to claim 5, further comprising:
(F) a step of collecting, prior to the step (A), the aerosol particles with a plurality of kinds of particle sizes suspended in the atmosphere; and
(G) a step of setting particle size groups as measurement targets among the plural kinds of particle sizes in a plurality of manners, and calculating the reference voltage value U for each of the set particle size groups, and
wherein in the step (B), the voltage values U calculated in the step (G) are initially set as the reference voltage in sequence.

7. The method according to claim 5,
wherein the step (C) includes:
(C-1) a step of splitting the aerosol particles classified out in the step (B) into two lines;
(C-2) a step of electrically measuring the aerosol particles by collecting electric charges on the aerosol particles split into one of the lines in the step (C-1), by using a Faraday cup aerosol electrometer (FCAE);
(C-3) a step of growing the aerosol particles split into the other line in the step (C-1) large by means of condensation, irradiating the grown aerosol particles with a laser beam, and optically measuring the aerosol particles by receiving scattered lights from the irradiated aerosol particles, by using a condensation particle counter (CPC); and
(C-4) a step of calibrating the CPC used in the step (C-3) by comparing the particle size distribution which is calculated in the step (E) based on a result of the measurement in the step (C-2) and the particle size distribution which is calculated in the step (E) based on a result of the measurement in the step (C-3).

8. The method according to claim 7,
wherein, in the step (C-4), for the calibration of the CPC, detection efficiency regarding the optical measurement in the step (C-3) is calculated based on the following relational expression (18'):

$$\eta_{CPC}(Z_1(U)) = \frac{M_{CPC}(Z_1(U)) - \sum_{p \geq 2}^{n} \alpha_p \cdot M_{CPC}(Z_1(pU))}{M_{FCAE}(Z_1(U)) - \sum_{p \geq 2}^{n} p \cdot \alpha_p \cdot M_{FCAE}(Z_1(pU))} \cdot \eta_{FCAE}(Z_1(U)) \qquad (18')$$

where
$\eta_{CPC}(Z_1(U))$ is the detection efficiency regarding the optical measurement in the step (C-3),
$\eta_{FCAE}(Z_1(U))$ is detection efficiency regarding the electrical measurement in the step (C-2),
p is a value regarding the number of times the measurement is executed in the step (C),
$\alpha_p$ is a value regarding a charging probability for the aerosol particles to be charged in the step (A) and regarding the p,
$M_{cpc}(Z_1(U))$ is the first measurement result output in the step (b-1) based on the measurement result in the step (C-2).
$M_{cpc}(Z_1(pU))$ is the re-measurement result, corresponding to the p, output in the step (b-2) based on the measurement result in the (C-3),
$M_{FCAE}(Z_1(U))$ is the first measurement result output in the step (b-1) based on the measurement result in the step (C-2), and
$M_{FCAE}(Z_1(pU))$ is the re-measurement result, corresponding to the p, output in the step (b-2) based on the measurement result in the step (C-2).

* * * * *